United States Patent
Ohmae et al.

(10) Patent No.: US 9,314,496 B2
(45) Date of Patent: Apr. 19, 2016

(54) INSOLUBLE DIETARY FIBER-CONTAINING PRODUCT DERIVED FROM GRAIN SEEDS

(75) Inventors: Hideo Ohmae, Gunma (JP); Hiroshi Murayama, Gunma (JP); Naohiro Takimoto, Gunma (JP); Yuji Sakamoto, Gunma (JP); Osamu Kanauchi, Gunma (JP); Mikio Katayama, Gunma (JP); Hiroyuki Watanabe, Gunma (JP); Yuta Komano, Gunma (JP)

(73) Assignee: KIRIN HOLDINGS KABUSHIKI KAISHA, Tokyo (JP)

( * ) Notice: Subject to any disclaimer, the term of this patent is extended or adjusted under 35 U.S.C. 154(b) by 1193 days.

(21) Appl. No.: 12/809,191

(22) PCT Filed: Dec. 19, 2008

(86) PCT No.: PCT/JP2008/073885
§ 371 (c)(1),
(2), (4) Date: Oct. 14, 2011

(87) PCT Pub. No.: WO2009/078495
PCT Pub. Date: Jun. 25, 2009

(65) Prior Publication Data
US 2012/0141455 A1    Jun. 7, 2012

(30) Foreign Application Priority Data

Dec. 19, 2007 (JP) .................................. 2007-327967
Nov. 20, 2008 (JP) .................................. 2008-297174

(51) Int. Cl.
| | | |
|---|---|---|
| *A61K 35/00* | (2006.01) | |
| *A61K 36/899* | (2006.01) | |
| *A23L 1/10* | (2006.01) | |
| *A23L 1/105* | (2006.01) | |
| *A23L 1/308* | (2006.01) | |
| *C12P 19/04* | (2006.01) | |
| *C12P 19/14* | (2006.01) | |

(52) U.S. Cl.
CPC .............. *A61K 36/899* (2013.01); *A23L 1/1016* (2013.01); *A23L 1/1055* (2013.01); *A23L 1/3081* (2013.01); *C12P 19/04* (2013.01); *C12P 19/14* (2013.01)

(58) Field of Classification Search
USPC ............. 424/115; 426/627, 590, 531, 18, 482
See application file for complete search history.

(56) References Cited

U.S. PATENT DOCUMENTS

| 5,622,738 A | 4/1997 | Takeuchi et al. |
|---|---|---|
| 6,348,221 B1 * | 2/2002 | Kanauchi ............. A23K 1/1631 424/115 |
| 6,475,533 B2 * | 11/2002 | Kanauchi et al. ............. 424/750 |
| 2005/0089602 A1 | 4/2005 | Kvist et al. |
| 2006/0147500 A1 | 7/2006 | Klingeberg et al. |
| 2006/0286186 A1 * | 12/2006 | Bird et al. ..................... 424/750 |
| 2008/0214656 A1 * | 9/2008 | Lim et al. ..................... 514/450 |

FOREIGN PATENT DOCUMENTS

| CN | 1840674 | 10/2006 |
|---|---|---|
| EP | 0369818 | 5/1990 |
| JP | 03-049662 A | 3/1991 |
| JP | 03-123479 A | 5/1991 |
| JP | 03-209331 A | 9/1991 |
| JP | 3007645 | 2/2000 |
| JP | 2002-275076 A | 9/2002 |
| JP | 2004-520058 A | 7/2004 |
| JP | 2006-124370 A | 5/2006 |
| JP | 2006-527586 A | 12/2006 |
| JP | 2008-189625 A | 8/2008 |
| WO | 02067698 | 9/2002 |
| WO | 2006/002495 A1 | 1/2006 |

OTHER PUBLICATIONS

CDC (Centers For Disease Control and Prevention). Inflammatory Bowel Disease. Downloaded from the CDC website on Nov. 28, 2013: <http://www.cdc.gov/ibd/>.*
WebMD. Crohn's Disease Prevention. Downloaded from the WebMD website on Nov. 28, 2013: <http://www.webmd.com/ibd-crohns-disease/crohns-disease/tc/crohns-disease-prevention>.*
Patent Examination Report for Australian Application No. 2008339365 dated Feb. 8, 2013.
Atsuhiro Ogawa et al., "Natural Immunity and Treatment of IBD," Modern Physician, Jul. 2007, pp. 892-895, vol. 27, No. 7.
Akira Ando et al., "Scientifically-Supported Food as a Therapeutic Method and Intestinal Bacteria Modulator—Focusing on the effects of dietary fiber", Clinical Gastroenterology, 2004, pp. 1749-1758, vol. 19, No. 13.

* cited by examiner

*Primary Examiner* — Kagnew H Gebreyesus
*Assistant Examiner* — Nghi Nguyen
(74) *Attorney, Agent, or Firm* — Sughrue Mion, PLLC

(57) ABSTRACT

This invention provides a product safe for treating, improving or preventing an inflammatory bowel disease such as ulcerative colitis, and provides a product comprising an insoluble dietary fiber obtained by enzymatic treatment of seeds of a grain plant(s) or germinated young seeds thereof, as well as a food or drink or medicament comprising the product.

22 Claims, 31 Drawing Sheets

INSOLUBLE DIETARY FIBER-CONTAINING PRODUCT DERIVED FROM GRAIN SEEDS

TECHNICAL FIELD

The present invention relates to a product or matter characterized by comprising an insoluble dietary fiber derived from grain or cereal seeds or germinated young seeds thereof, and to methods for producing the same. More specifically, the present invention relates to food products for improving inflammatory activities of the intestinal tract and to methods for producing the same.

BACKGROUND ART

As a disease of an unknown cause derived from inflammation of the intestinal tract, Crohn disease and ulcerative colitis are known. Ulcerative colitis is a chronic and diffuse colic disorder with a severe bloody diarrhea and abdominal pain as major complaints and repeated remission and recurrence. With westernization of daily diet in recent years, the number of the patients has been increased. From this, it is considered that diet and ulcerative colitis are closely associated with each other. There are many hypotheses on the cause of the disorder; however the cause has not yet been elucidated. Presently, the number of patients suffered from inflammatory bowel disease exceeds about 90,000 in Japan. In the United State, the number of patients with the disorder has been increased from 100,000 to about 100,000,000 during the latest 10 years. In consideration of this, it is presumed that the number of patients will significantly increase also in Japan.

Ulcerative colitis is basically treated by medical therapy; however, a definitively useful therapeutic medicine has not so far been developed. A 5-Aminosalicylic acid (5-ASA) preparation, an adrenocorticosteroid agent, a blood cell component removing therapy, and an immune suppressor are used.

In either one of the therapeutic methods, side effect is a matter of concern. A 5-aminosalicylic acid preparation sometimes causes nausea, fever, headache, abdominal pain and diarrhea, in general. Furthermore, an adrenocorticosteroid agent generally tends to cause infectious diseases and side effects such as elevation of a blood glucose level in diabetes have been reported, causing severe anxiety in patients.

It is known that ulcerative colitis is induced by administering dextran sulfate sodium to a mouse or rat, which is used as an experimental ulcerative colitis model. In mice administered with dextran sulfate sodium, ulcerative colitis is induced, leading to inflammation in the intestinal tract. As a result, the phenomena that the large intestine shrinks and the epithelial cells are sloughed off from the intestinal tract are observed, and the mice fall in the state of severe diarrhea. Thereafter, the body weights of the mice reduce and some of mice collapse to die.

Examples of food component materials effective for inflammatory bowel disease include acidic xylooligosaccharide obtained by treating wood chips with hemicellulase (Japanese Patent Publication (Kokai) No. 2007-230998 A), galactomannan and arabinogalactan (International Publication No. WO 05/056022), plant-derived proanthocyanidin (Japanese Patent Publication (Kokai) No. 2007-77122 A), and proteins and insoluble dietary fiber derived from germinated seeds of a Gramineae plant (Japanese Patent Publication (Kokai) No. 2005-232178 A). Furthermore, there are reports that cereals are treated with hemicellulase and its insoluble residual fraction is imparted with a function as food. Such reports include an antiulcer agent obtained by treating bran with hemicellulase (Japanese Patent Publication (Kokai) No. 2006-124370 A); a dietary fiber material for patients with kidney disease obtained by treating wheat bran with hemicellulase (Japanese Patent Publication (Kokai) No. 06-70720 A (1994)); a method of obtaining a fraction rich in aleurone protein from the purified bran which comprise a seed coat fraction and an aleurone fraction and which is obtained from cereal bran by enzymatic treatment and wet pulverizing, and use of the fraction in food and feed (Japanese Patent Publication (Kohyo) No. 2004-520058 A). However, there are no reports on the effect of improving, treating or preventing an inflammatory bowel disease.

DISCLOSURE OF THE INVENTION

An object of the present invention is to provide a material capable of being safely used in overcoming the above problem, for example, improving an inflammatory bowel disease. Another object of the present invention is to provide a food or drink and a medicament comprising the material.

The present inventors repeatedly conducted extensive studies in order to solve the above-described problem. As a result, the present inventors have now found that an insoluble fraction containing an insoluble dietary fiber (hereinafter also referred to as a "insoluble dietary fiber-containing product"), which is prepared by removing starch from seeds of a grain plant(s), preferably, seeds of a Gramineae plant(s), and treating the remaining fruit skin, seed coat or the like with hemicellulase, can attain the above objects. Based on the finding, the present invention was accomplished. The gist of the present invention is as follows.

(1) An insoluble dietary fiber-containing product derived from seeds of a grain plant(s) and produced by a process comprising the following steps of: (a) preparing a raw-material by pulverizing or polishing the seeds of the grain plant(s) then recovering the resultant outer fraction of the seeds; (b) subjecting the raw material to a starch removing treatment to prepare a starch-free fraction; (c) enzymatically treating the fraction prepared in the step (b) with an enzyme having hemicellulase activity; and (d) recovering an insoluble fraction from the enzymatically treated solution.

(2) The insoluble dietary fiber-containing product according to the above (1), wherein the grain plant is a Gramineae plant.

(3) The insoluble dietary fiber-containing product according to the above (2), wherein the Gramineae plant is rice, barley, rye or wheat.

(4) The insoluble dietary fiber-containing product according to the above (1), wherein, in the step (b), the starch removing treatment is carried out by an enzyme treatment using an amylase or a glucoamylase.

(5) The insoluble dietary fiber-containing product according to the above (1), wherein, in the step (b), the starch removing treatment is carried out by a heat gelatinization treatment.

(6) The insoluble dietary fiber-containing product according to the above (1), wherein, in the step (b), the starch removing treatment is carried out by a physical destruction treatment.

(7) The insoluble dietary fiber-containing product according to the above (6), wherein the physical destruction treatment is carried out by a homogenizer.

(8) The insoluble dietary fiber-containing product according to the above (1), wherein, in the step (b), the starch-free fraction is further subjected to a press-peeling treatment.

(9) The insoluble dietary fiber-containing product according to the above (1), wherein the raw material to be subjected to the starch removing treatment is rice bran, wheat malt, or barley malt.

(10) The insoluble dietary fiber-containing product according to the above (1), wherein the raw material to be subjected to the starch removing treatment is fat-free rice bran.

(11) The insoluble dietary fiber-containing product according to the above (8), wherein the raw material to be subjected to the starch removing treatment is wheat bran or polished-barley residue.

(12) The insoluble dietary fiber-containing product according to the above (8), wherein the starch-free fraction is brewer's grains.

(13) The insoluble dietary fiber-containing product according to any one of the above (1) to (12), wherein the enzyme having a hemicellulase activity is xylanase.

(14) The insoluble dietary fiber-containing product according to any one of the above (1) to (13), wherein, in the step (c), the enzyme is used in combination with a protease.

(15) The insoluble dietary fiber-containing product according to any one of the above (1) to (14), wherein, after the step (c), a defatting treatment is further comprised.

(16) The insoluble dietary fiber-containing product according to any one of the above (1) to (15), wherein the insoluble fraction in the step (d) includes a fraction having a grain size which substantially passes through a 5 to 25 mesh ASTM (American Society for Testing and Materials) standard sieve and does not pass through a 500 mesh ASTM standard sieve.

(17) The insoluble dietary fiber-containing product according to the above (16), wherein the insoluble fraction in the step (d) includes a fraction having a grain size, which does not substantially pass through a 200 mesh ASTM standard sieve.

The insoluble dietary fiber-containing product according to any one of the above (1) to (17), wherein the insoluble dietary fiber-containing product has a protein content of 20 wt % or less and a dietary fiber content of 55 wt % or more.

(19) The insoluble dietary fiber-containing product according to any one of the above (1) to (18), wherein the insoluble dietary fiber-containing product contains the insoluble dietary fiber in which an aleurone layer is partially or completely removed.

(20) An insoluble dietary fiber-containing product derived from grain plant seeds, wherein the insoluble dietary fiber-containing product has the following properties of:

(i) that the insoluble dietary fiber-containing product comprises a fraction having a grain size which substantially passes through a 5 to 25 mesh ASTM (American Society for Testing and Materials) standard sieve and does not pass through a 500 mesh ASTM standard sieve; (ii) that the insoluble dietary fiber-containing product has a protein content of 20 wt % or less and a dietary fiber content of 55 wt % or more; (iii) that aleurone layer of the insoluble dietary fiber is partially or completely removed; and (iv) that the insoluble dietary fiber-containing product has a prevention and/or improvement effect on ulcerative colitis.

(21) The insoluble dietary fiber-containing product according to the above (20), comprising a fraction having a grain size which does not substantially pass through a 200 mesh ASTM standard sieve.

(22) The insoluble dietary fiber-containing product according to any one of the above (1) to (21), having an improvement, treatment or prevention effect on an inflammatory bowel disease.

(23) The insoluble dietary fiber-containing product according to the above (22), wherein the inflammatory bowel disease is ulcerative colitis.

(24) The insoluble dietary fiber-containing product according to any one of the above (1) to (23), incorporated in a food or drink or a pharmaceutical preparation.

(25) The insoluble dietary fiber-containing product according to the above (24), incorporated in a functional food.

(26) Use of the insoluble dietary fiber-containing product according to any one of the above (1) to (25), in the manufacture of a food or drink or a medicament for treatment, improvement or prevention of an inflammatory bowel disease.

(27) A method for producing an insoluble dietary fiber-containing product derived from seeds of a grain plant(s), wherein the insoluble dietary fiber-containing product is produced by a process comprising the following steps of: (a) preparing a raw material by pulverizing or polishing the seeds of the grain plant(s) then recovering the resultant outer fraction of the seeds; (b) subjecting the raw material to a starch removing treatment to prepare a starch free fraction; (c) enzymatically treating the fraction prepared in the step (b) with an enzyme having hemicellulase activity; and (d) recovering an insoluble fraction from the enzymatically treated solution.

(28) A method for producing the insoluble dietary fiber-containing product according to the above (20), comprising the following steps of: (a1) preparing a raw material by pulverizing or polishing seeds of a grain plant(s) then recovering the obtained outer fraction of the seeds; (b1) subjecting the raw material to a starch removing treatment by physical destruction to prepare a starch free fraction; and (e1) recovering, from the fraction prepared in the step (b1), an insoluble fraction which passes through a 5 to 25 mesh ASTM (American Society for Testing and Materials) standard sieve and does not pass through a 500 mesh ASTM standard sieve.

The specification comprises the contents described in the specifications and/or drawings of Japanese Patent Applications No. 2007-327967 and No. 2008-297174 from which the present application claims the priority.

BEST MODE FOR CARRYING OUT THE INVENTION

Figure 1:
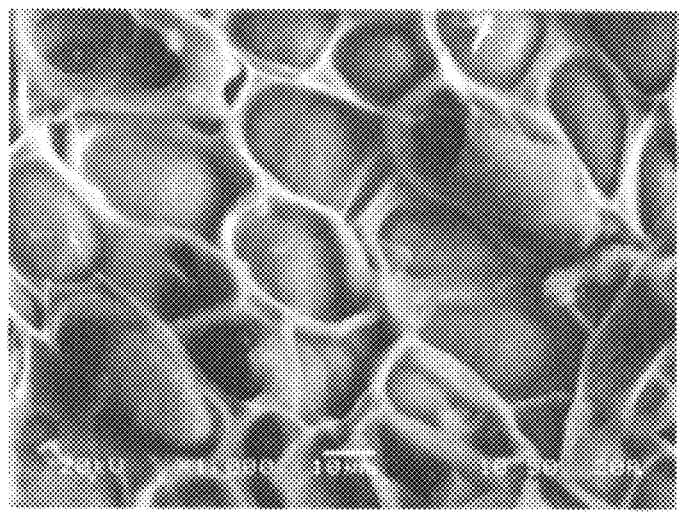
FIG. 1 shows the photograph of an aleurone layer portion contained in Preparation Sample 1.

Hereinafter, the insoluble dietary fiber-containing product, the method for producing the same, and the food or drink and the pharmaceutical preparation (or medicament) of the present invention will be described.

The insoluble dietary fiber-containing product of the present invention is characterized by containing an insoluble dietary fiber derived from seeds of a cereal plant(s), preferably a Gramineae plant(s).

Examples of the Gramineae plant(s) that can be used in the present invention include all plants classified in Gramineae plants listed in the plant classification table. Specific examples include, but not limited to, rice, barley, wheat, rye, foxtail millet, Japanese millet and corn. Of them, rice, barley, rye and wheat are preferably used.

The insoluble dietary fiber-containing product of the present invention can be produced by removing, e.g., starch from seeds of a grain plant(s), preferably a Gramineae plant(s), as a raw material, subjecting the obtained starch etc-free fraction to an enzyme treatment, and recovering the resulting insoluble fraction.

Specifically, the insoluble dietary fiber-containing product can be produced by a process comprising: (a) a step of preparing a raw material by pulverizing or polishing seeds of a grain plant(s) then recovering the obtained outer fraction of the seeds; (b) subjecting the raw material to a starch removing treatment to prepare a starch-free fraction; (c) enzymatically treating the fraction prepared in the step (b) with an enzyme having hemicellulase activity; and (d) recovering an insoluble fraction from the enzymatically treated solution.

The step (a) includes pulverizing and/or polishing grain plant seeds to obtain a raw material for preparing the insoluble dietary fiber-containing product of the present invention. The pulverization can be performed by, for example, a roll mill, a disk mill and a hammer mill. Furthermore, the polishing means removing and separating fruit skin, seed coat, germ, etc. from the grain plant seeds. This is performed by a machine principally peeling the surface of a material, for example, a rice mill or a stone mill. When polishing is performed, a seed outer fraction including fruit skin, seed coat and germ produced by such a treatment can be used as a raw material in the step (b). This step may include a threshing treatment other than pulverization and/or polishing of grain plant seeds when the seeds have husk. Furthermore, the grain plant seeds to be used may be either germinated or ungerminated.

The step (a) can be omitted when a material already treated in substantially the same manner is used as a raw material. Examples of such a material include, but not limited to, bran secondarily produced when wheat powder is produced and rice bran secondarily produced after rice is polished. Use of such a material is preferred since starch is already removed mostly from grain plant seeds and the step can be simplified. When rice bran is used as a raw material, it is preferred to use fat-free rice bran produced after a defatting treatment is applied to rice bran. This is because the fat-free rice bran is a more inexpensive material than rice bran and has an excellent flavor. In addition, compared to the case where the same amount of rice bran is used, a larger amount of insoluble dietary fiber-containing product can be advantageously obtained.

The step (b) includes removing starch from the raw material prepared in the step (a) to prepare a starch-free fraction. Any method may be employed as the starch removing treatment as long as it can remove starch from the raw material. For example, a starch removing treatment can be performed by an enzymatic starch decomposition treatment, heat gelatinization followed by sieving, or a starch removing treatment by physical destruction.

When the starch removing treatment is performed by saccharification treatment using an enzyme, an amylase or a glucoamylase enzyme can be employed but not limited to these. Examples of the amylase and glucoamylase that can be used in the present invention include, but not limited to, a commercially available enzyme preparation such as Orientase (trade name, manufactured by HBI Inc.), Kokugen (trade name, manufactured by Daiwa Fine Chemicals Co., Ltd.), Sumiteam (trade name, manufactured by Shinnihon Chemicals Corporation), Termamyl (trade name, manufactured by Novozymes) and Gluczyme (trade name, manufactured by Amano Enzyme Inc.), and amylases and glucoamylases produced by microorganisms belonging to the genera *Trichoderma* sp., *Thermomyces* sp., *Aureobasidium* sp., *Streptomyces* sp., *Aspergillus* sp., *Clostridium* sp., *Bacillus* sp., *Thermotogae* sp., *Thermoascus* sp., *Caldocellum* sp., *Thermomonospora* sp., *Humicola* sp., *Rhizopus* sp., and *Penicillium* sp., for example. The aforementioned enzymes usable in the present invention may be present in any forms such as a purified enzyme, a crude enzyme and an immobilized enzyme, as long as they maintain an enzymatic activity. The immobilized enzyme is an enzyme attached to a carrier such as a polymer, a polysaccharide and an inorganic material. Examples of the crude enzyme include an enzyme-containing extract derived from an enzyme-containing microorganism and a processed product such as a dry material. Furthermore, the saccharification treatment is performed generally at a temperature of 10 to 90° C., preferably 30 to 60° C., at a pH of 3 to 10, preferably 5 to 7. It is preferred that saccharification is performed at an optimal temperature, or at an optimal pH, of the amylase and glucoamylase to be used. The time for the enzyme treatment can be 30 minutes to overnight, for example, 3 hours. Note that the amount of an added enzyme can be determined by those skilled in the art depending upon the amount of the raw material prepared.

The heat gelatinization can be performed by use of the phenomenon that, when starch is suspended in water and heated, starch particles absorb water, gradually swell and finally collapse and are dissolved. Thereafter, the gelatinized starch can be removed by solid-liquid separation by means of a sieve.

The starch removing treatment by physical destruction can be performed by using, for example, a homogenizer, a high-speed mixer, a homo mixer, or a stirrer. Not only starch but also a part of an aleurone layer can be removed by the starch removing treatment by physical destruction.

When germinated seeds can be used as the grain plant seeds, the starch removing treatment can be performed simply by heating without externally adding an amylase or a glucoamylase. This is because germinated seeds themselves produce an amylase in this case.

In the production method of the present invention, a material, to which substantially the same treatments as in the steps (a) and (b) have been applied, may be used as a starch-free fraction in the following steps. Examples of such a material include, but not limited to, brewer's grains, which are barley malt generated when beer is produced. It is preferred to use such a material since most of starch is already removed and in view of simplification of the step.

The starch free fraction prepared by the step (b) may contain not only main components such as an aleurone layer, fruit skin and seed coat but also husk, germ, other proteins and lipid, etc. The plant tissues of the aleurone layer, fruit skin and seed coat of malt are shown in Barley: Chemistry and Technology edited by Alexander W. MacGregor et al., p 46, FIG. 8. Furthermore, these are commonly present in seeds of Gramineae plants as shown in Journal of Cereal Science 36 (2002) 261-284.

The step (b) may further include a press-peeling treatment of a starch-free fraction. The press-peeling treatment refers to a treatment of passing a multi-layer composition in an appropriate slit between two roll mills rotated at slightly different rotational speeds, to apply force in parallel to the pressed surface, thereby peeling a part of the layer. In the press-peeling treatment, any pulverizer can be used as long as it has a structure of applying compression force to the raw material to be treated. For example, in the press-peeling treatment, other than the roll mills different in rotational speed, a mortar-form pressurizing treatment apparatus having a slit and controlled in rotational speed can be used. Particularly, a roll mill is desirably used. At this time, the slit between the rolls is set to 0.15 to 0.01 mm, preferably, 0.08 to 0.02 mm. The size is selected such that physical pulverization can be efficiently applied to a multi-layered composition. In this manner, the aleurone layer contained in a starch-free fraction is exposed, with the result that a hemicellulase removal treatment of an aleurone layer in the step (c) can be efficiently performed. Particularly, the press-peeling treatment has now been found to definitely influence the improvement effect of the insoluble dietary fiber-containing product of the present invention finally obtained upon an inflammatory bowel disease, depending upon the raw material and the starch-free fraction to be used. When such a raw material or a starch-free fraction is used, the press-peeling treatment is preferably performed in the step (b) accordingly. Examples of the raw material or starch-free fraction preferably subjected to a press-peeling treatment include wheat bran, polished-barley residue and brewer's grains. On the other hand, there is a raw material finally providing an insoluble dietary fiber-containing product of the present invention, which exerts an effective improvement effect on an inflammatory bowel disease, even if a press-peeling treatment may not be performed. Examples of such a raw material include rice bran, fat-free rice bran, wheat malt and barley malt. Furthermore, when germinated seeds are used as grain plant seeds, it is suggested that such a press-peeling treatment can be omitted.

The step (b) may further include a sieving treatment of a starch-free fraction performed in the presence of water. The sieving treatment is performed in order to remove husk and other materials such as undesirable materials contained in a starch-free fraction in a large amount, thereby roughly separating a fraction (hereinafter also referred to as fruit skin/seed coat fraction) mainly containing an aleurone layer, fruit skin and seed coat. The sieving treatment can be performed by, for example, allowing a starch-free fraction to pass through a mesh having an appropriate mesh size and removing the fraction remaining on the mesh. The mesh size of the sieve to be used in the sieving treatment sometimes varies depending upon the raw material and starch-free fraction to be used. Generally, ASTM (American Society for Testing and Materials) standard sieves of 5 to 25 mesh, for example, 12 mesh, 16 mesh or 20 mesh, can be used. This treatment is preferred in view of handling in the subsequent operations since a large amount of undesirable materials can be removed.

In the step (b), the press-peeling treatment and the sieving treatment are preferably used in combination. In this case, the combination treatments are preferably performed repeatedly in combination, 2 to 5 times. This is because a fraction containing an aleurone layer, fruit skin or seed coat as a main component can be efficiently obtained by these treatments.

As mentioned above, it has now been found that presence or absence of a pretreatment such as press-peeling treatment sometimes influences the inflammatory bowel disease improvement effect of the insoluble dietary fiber-containing product of the present invention finally obtained, depending upon the type of grain plant seeds to be used, its germinated state and the type of raw material. Thus, the steps (a) and (b) can be defined as pretreatments for the step (c), which is an enzyme treatment step for efficiently performing decomposition of the aleurone layer with hemicellulase. Therefore, the starch-free fraction to be subjected to the step (c) is preferably confirmed as to whether it is suitably pretreated in the steps (a) and (b) before subjected to step (c), and, if necessary, a pretreatment such as a press-peeling treatment is preferably added or repeated. At this time, a tissue of the starch free fraction prepared, for example, in the steps (a) and (b) is microscopically observed or analyzed by use of an iodine starch reaction. In this way, whether the fraction is suitably pretreated or not is conceivably determined.

The step (c) includes removing the aleurone layer contained in a starch-free fraction or a fruit skin/seed coat fraction prepared in the step (b), as described above. This step includes an enzyme treatment of a starch-free fraction or a fruit skin/seed coat fraction with an enzyme having a hemicellulase enzymatic activity. Examples of the enzyme having a hemicellulase enzymatic activity that can be used in this step include, but not limited to, 13-glucosidase, cellulase, xylosidase, xylanase, mannosidase, mannanase, arabinosidase, arabanase, pectinase and glucanase. Particularly, a xylan-decomposing enzyme including xylanase is preferably used. Specific examples of hemicellulase that can be used in the present invention include, but not limited to, commercially available enzyme preparations such as Cellulosin (trade name, manufactured by HBI Inc.), Multifect 720 (trade name, manufactured by Genencor Kyowa), Sumiteam (trade name, manufactured by Shinnihon Chemicals Corporation), Pentopan (trade name, manufactured by Novozymes) and hemicellulase "Amano" 90 (trade name, manufactured by Amano Enzyme Inc.); and xylanase produced by microorganisms belonging to the genera Trichoderma sp., Thermomyces sp., Aureobasidium sp., Streptomyces sp., Aspergillus sp., Clostridium sp., Bacillus sp., Thermotogae sp., Thermoascus sp., Caldocellum sp., Thermomonospora sp., Humicola sp., Rhizopus sp. and Penicillium sp., for example. The aforementioned enzymes to be used in the present invention can be used in any forms such as a pure enzyme, a crude enzyme and an immobilized enzyme as long as it maintains an enzymatic activity. The immobilized enzyme is an enzyme attached to a carrier such as a polymer, a polysaccharide and an inorganic material. Examples of the crude enzyme include an enzyme-containing extract from an enzyme-containing microorganism and a processed product such as a dry material. The enzyme treatment with hemicellulase is generally performed at a temperature of 10 to 90° C., preferably 30 to 60° C., at a pH of 3 to 10, preferably 5 to 7; however, it is preferred that the enzyme treatment is performed at an optimal temperature or an optimal pH of hemicellulase enzyme to be used. Furthermore, the time for an enzyme treatment can be set to 30 minutes to overnight. Note that the amount of the enzyme can be set by those skilled in the art depending upon the amount of the starch-free fraction or fruit skin/seed coat fraction prepared. It is possible to visually confirm by e.g., a fluorescent microscope or an electron microscope that the aleurone layer of a starch-free fraction or a fruit skin/seed coat fraction is partially or completely removed after the enzyme treatment with hemicellulase. Confirmation can be made by using the fluorescent microscopic analysis in accordance with an analytical method such as a method generally known to those skilled in the art as described in "PLANT MICROTECHNIQUE AND MICROSCOPY" written by STEVEN E. RUZEN, Chapter 7 (pp. 87-119). Furthermore, confirmation can be made by an electron-microscopic analysis method such as a method generally used by those skilled in the art.

In the enzyme treatment of step (c), a protease treatment is preferably combined. By this method, the amount of an enzyme having hemicellulase enzymatic activity, which decomposes the aleurone layer, can be reduced to an amount of ⅕ to 1/10 fold when compared to the case where the enzyme used alone. It is favorable in cost performance.

The step (c) preferably includes a defatting treatment performed after the hemicellulase treatment. By virtue of this, the taste and quality of the insoluble dietary fiber-containing product of the present invention can be improved. The defatting method is not particularly limited to a specific method; however, for example, the defatting is performed by a treatment using a solvent(s) such as ethanol, acetone or hexane. These techniques are obvious to those skilled in the art. It should be noted that when defatted rice bran is used as a raw material to be subjected to the starch removing treatment, even if such a defatting treatment is not performed, the aforementioned benefit can be obtained.

The step (d) is a step of recovering an insoluble fraction from the enzymatically treated solution in the step (c). Preferably, an insoluble fraction that passes through a 5 to 25 mesh ASTM standard sieve and does not pass through a 500 mesh ASTM standard sieve, is recovered in this step. The fraction having a particle-size distribution passing through 500 mesh does not have the advantageous effect of the present invention as described later (see [Results of Test Example 10]). In this step, it is particularly important for obtaining a higher effect to obtain a fraction that does not pass through a 500 mesh ASTM standard sieve. More specifically, the sieving treatment can be performed by a two-step system. That is, a hemicellulase treatment solution is sieved using a first mesh and the fraction passed through the sieve is sieved using a second mesh, which has a smaller mesh size than the first mesh. The insoluble dietary fiber-rich insoluble fraction remaining on the sieve (more specifically, "insoluble dietary fiber-containing product") is recovered. The mesh sizes of the first and second meshes to be used in the sieving treatment are not particularly limited as long as the fraction having the aforementioned particle-size distribution can be recovered. For example, as the first mesh, a 5 to 25 mesh ASTM standard sieve, for example, a 12 mesh or a 16 mesh, preferably, a 20 to 25 mesh (sieve) is selected and as the second mesh, a 50 to 500 mesh ASTM standard sieve can be selected. By virtue of the sieving treatment, a desired fraction in the enzymatically treated solution can be obtained.

It is further preferable that the insoluble fraction recovered in the step (d) is a fraction that does not pass through a 200 mesh ASTM standard sieve. This is because when the fraction having a grain size that does not pass through a 500-mesh ASTM standard sieve is compared to the fraction having a grain size that does not pass through a 200-mesh ASTM standard sieve, the fraction having a grain size that does not pass through a 200-mesh ASTM standard sieve is demonstrated to have a higher effect (see [Results of Test Example 9]).

Note that, in the step (b), when the fruit skin/seed coat fraction is already roughly fractioned, it is not necessary to perform the step (d) by the two step system. The fraction remaining on the sieve by the sieving treatment using the second mesh may be recovered.

The insoluble fraction obtained in the step (d) is usually dried by lyophilization or the like, and can be used as the insoluble dietary fiber-containing product of the present invention, preferably without applying further processing such as pulverizing into fine particles.

The insoluble dietary fiber-containing product of the present invention thus produced is composed of the fraction that passes preferably through substantially a 5 to 25 mesh ASTM standard sieve and does not pass through a 500 mesh ASTM standard sieve based on the sieving treatment of the step (d). The term "substantially" as used herein is intended to mean that an insoluble dietary fiber-containing product contaminated with a small amount of components outside the above grain size range falls within the scope of the invention. Accordingly, the insoluble dietary fiber-containing product of the present invention composed of the fraction having a grain size which substantially passes through a 5 to 25 mesh ASTM standard sieve and does not pass through a 500 mesh ASTM standard sieve contains the aforementioned grain size fraction in amount of at least 90% or more, preferably 91%, 92%, 93%, 94%, 95%, 96%, 97%, 98% or 99%, and most preferably 100%.

Furthermore, the insoluble dietary fiber-containing product of the present invention preferably has the property of having a protein content of 20 wt % or less and an insoluble dietary fiber content of 55 wt % or more. The protein content used herein is obtained from a numerical value provided by multiplying a nitrogen content obtained by use of the Kjeldahl method by a protein conversion coefficient, 6.25. The dietary fiber content is obtained based on the AOAC method.

Furthermore, in the insoluble dietary fiber contained in the insoluble dietary fiber-containing product of the present invention, the aleurone layer is partially or completely removed. The term "partially" as used herein means that 70% or more of the aleurone layer of the insoluble dietary fiber, preferably 80% or more, more preferably 90% or more, more preferably 95% or more, most preferably 99% or more is removed. The aleurone layer of the insoluble dietary fiber is preferably completely removed.

The fact that the aleurone layer of the insoluble dietary fiber is partially or completely removed can be visually confirmed by e.g., a fluorescent microscope or an electron microscope as mentioned above or alternatively, confirmed by, for example, subjecting the insoluble dietary fiber-containing product of the present invention to an enzyme treatment with hemicellulase and evaluating the recovery rate after the treatment. Since the insoluble dietary fiber-containing product of the present invention is a fraction from which an aleurone layer is mostly removed as described above, even if the fraction is subjected again to the enzyme treatment with hemicellulase, the recovery rate after the treatment is extremely high. More specifically, the insoluble dietary fiber-containing product of the present invention is characterized by providing a recovery rate of at least about 70% or more, preferably, at least about 80% or more, when it is subjected again to the enzyme treatment with hemicellulase in a 50 mM acetate buffer (pH 4.5, 50° C.) containing a 4.0% hemicellulase preparation (Sumiteam NX manufactured by Shinnihon Chemicals Corporation) overnight. Note that the term "recovery rate" as used herein is a relative value of a material, which is obtained by subjecting the obtained insoluble dietary fiber-containing product obtained again to the enzyme treatment (4.0% hemicellulase, pH 4.5, 50° C., overnight) and then subjecting to lyophilization, relative to the weight of the obtained insoluble dietary fiber-containing product obtained as 100%.

The insoluble dietary fiber-containing product of the present invention has other features. For example, swelling ability can be mentioned. The swelling ability as used herein is the feature that water molecules are incorporated into the insoluble dietary fiber-containing product (within the plant tissue) and the particles of the product are swollen and increase in size. The swelling ability that the insoluble dietary fiber-containing product of the present invention has can be confirmed, for example, by weighing a predetermined amount of the insoluble dietary fiber-containing product into a volumetric graduated cylinder, adding a predetermined volume of water to the cylinder, allowing to stand still for a predetermined time, and determining the degree of swelling by graduation of the graduated cylinder. The swelling ability of the insoluble dietary fiber-containing product of the present invention can be characterized by a swelling volume of at most 20-35 ml per gram.

Production of the insoluble dietary fiber-containing product of the present invention will be more specifically described below by way of the case where brewer's grains are used as a starch-free fraction and wheat bran or rice bran are used as a raw material.

When the insoluble dietary fiber-containing product of the present invention is produced, it is economically preferable to use e.g., brewer's grains, i.e. the starch-free barley malt, which is generated during beer production, and bran, which is secondarily produced when wheat powder is produced, or rice bran, which is secondarily produced after rice is polished, as described above.

When brewer's grains are used in producing the insoluble dietary fiber-containing product of the present invention, the insoluble dietary fiber-containing product of the present invention can be obtained by a method specifically described, for example, in JP Patent Publication (Kokoku) No. 4-31666 B (1992) can be used. More specifically, wet brewer's grains are pulverized under pressure and the resultant pressurized and pulverized material is sieved in the presence of water to prepare a fraction containing fruit skin/seed coat and aleurone layer in large amounts. The fraction may be treated with hemicellulase.

More specifically, to remove husk intrinsic to barley, wet-state brewer's grains are subjected to a press-peeling treatment. In the press-peeling treatment for brewer's grains, any pulverizer can be used as long as it has a structure of applying compression force to the raw material to be treated; however, particularly, a roll mill is desirably used. The interval between rolls is 0.15 to 0.01 mm, preferably 0.08 to 0.02 mm; however, the size is selected such that physical destruction of the multilayered material to be removed can be efficiently performed. When brewer's grains are subjected to a press-peeling treatment, it is desirable to adjust the moisture content of the brewer's grains to 65% or more. Next, the resultant press-peeled material is subjected to a sieving treatment performed in the presence of water. By virtue of the sieving treatment, a husk fraction remains on the sieve, whereas an aleurone layer-rich fruit skin/seed coat fraction passes through the sieve. The dimension of the sieve mesh is a 5 to 20 mesh ASTM standard sieve, preferably, 16 to 20 mesh. By the treatment above, a fraction containing husk intrinsic to barley in a large amount can be removed. Furthermore, to efficiently obtain the fruit skin/seed coat fraction, sieving is further performed by using a sieve of a smaller mesh size than that previously used. At this time, since the fruit skin/seed coat fraction remains on the sieve, the fruit skin/seed coat fraction can be prepared. The dimension of the sieve mesh secondarily used is set to a 50 to 200 mesh ASTM standard sieve. The press-peeling treatment and the sieving treatment are preferably repeatedly performed 2 to 5 times. The fruit skin/seed coat fraction obtained as mentioned above is subjected to a hemicellulase treatment and is subsequently sieved again using the 50 to 200 mesh ASTM standard sieve to remove substances decomposed by hemicellulase. The insoluble fraction remaining on the sieve is a desired insoluble dietary fiber-containing product. The insoluble dietary fiber-containing product obtained in this manner is usually dried and then put in use. The drying method includes, but is not limited to a lyophilization method.

When wheat bran is used for producing the insoluble dietary fiber-containing product of the present invention, first dry wheat bran is suspended in a solution containing an amylase or a glucoamylase to remove starch, thereby decomposing starch. After an amylase reaction is performed for a long time (for example, 30 minutes to overnight), a press-peeling treatment is performed using, for example, a roll mill, in order to efficiently perform an enzyme treatment with hemicellulase. The interval between rolls is 0.15 to 0.01 mm, preferably 0.08 to 0.02 mm; however, the size is selected such that physical destruction of the multilayered material to be removed can be efficiently performed. Next, sieving is performed using a 50 to 200 mesh ASTM standard sieve, preferably a 200 mesh ASTM standard sieve to remove amylase-decomposed substances, and the fruit skin/seed coat fraction remaining on the sieve is recovered. Next, this fraction is suspended in a solution containing hemicellulase and reacted for a long time (for example, 30 minutes to overnight). After completion of the reaction, sieving is performed using a 50 to 200 mesh ASTM standard sieve, preferably, a 200 mesh ASTM standard sieve, in the same manner to remove hemicellulase-decomposed substances and the insoluble fraction remaining on the sieve is recovered as the insoluble dietary fiber-containing product of the present invention. The insoluble dietary fiber-containing product obtained in this manner is usually dried and put in use. The drying method includes, but is not limited to, a lyophilization method.

When rice bran is used for producing the insoluble dietary fiber-containing product of the present invention, first, dry rice bran is suspended in a solution containing an amylase or a glucoamylase to remove starch, thereby decomposing starch. After an amylase reaction is performed for a long time (for example, 30 minutes to overnight), sieving is performed using a 50 to 200 mesh ASTM standard sieve, preferably a 200 mesh ASTM standard sieve, to remove amylase-decomposed substances and the fruit skin/seed coat fraction remaining on the sieve is recovered. Then, the recovered fraction is suspended in a solution containing hemicellulase and reacted for a long time (for example, 30 minutes to overnight). After completion of the reaction, sieving is performed using a 50 to 200 mesh ASTM standard sieve, preferably a 200 mesh ASTM standard sieve, to remove hemicellulase-decomposed substances and the fraction remaining on the sieve is recovered as the insoluble dietary fiber-containing product of the present invention. The insoluble food-containing product obtained in this manner is usually dried and put in use. The drying method includes, but is not limited to, a lyophilization method.

In the foregoing, the insoluble dietary fiber-containing product of the present invention and the method for producing the same have been described; however, the production method of the insoluble dietary fiber-containing product of the present invention is not limited to the above-described methods. More specifically, as long as an insoluble dietary fiber-containing product having the following properties (i) to (iv) can be produced from grain plant seeds, other production methods may be employed. The properties are: (i) that the insoluble dietary fiber-containing product comprises a fraction having a grain size which substantially passes through a 5 to 25 mesh ASTM standard sieve and does not pass through a 500 mesh ASTM standard sieve; (ii) that the insoluble dietary fiber-containing product has a protein content of 20 wt % or less and a dietary fiber content of 55 wt % or more; (iii) that the aleurone layer of the insoluble dietary fiber is partially or completely removed; and (iv) that the insoluble dietary fiber-containing product has a prevention and/or improvement effect on ulcerative colitis. Note that the prevention and/or improvement effect on ulcerative colitis will be described later.

An example of the alternative method of producing the insoluble dietary fiber-containing product of the present invention having the aforementioned features includes a method including the following steps of: (a1) preparing a raw material by pulverizing or polishing seeds of a grain plant(s) then recovering the obtained outer fraction of the seeds; (b1) subjecting the raw material to a starch removing treatment by physical destruction to prepare a starch free fraction; and (c1) recovering from the fraction prepared in the step (b1), an insoluble fraction that substantially passes through a 5 to 25 mesh ASTM (American Society for Testing and Materials) standard sieve and does not pass through a 500 mesh ASTM standard sieve.

This method can also be performed in the same manner as above, excepting that the starch removing treatment including physical destruction and the enzyme treatment step with an enzyme having hemicellulase activity are not comprised therein.

In such method, the starch removing treatment by physical destruction can be performed by a treatment using, for example, a homogenizer, a high-speed mixer, a homo mixer, or a stirrer. In this manner, the aleurone layer can be removed simultaneously with removal of the starch.

The starch removing treatment is preferably performed a plurality of times, for example, 2 to 5 times, in combination with a sieving treatment described in the above method, step (b). In this manner, the removal of starch and the accompanying aleurone layer removal can be more efficiently performed.

The starch removing treatment may be performed in combination with other starch removing treatments excluding physical destruction, for example, enzymatic starch decomposition treatment, heat gelatinization, and gelatinization followed by sieving.

The insoluble dietary fiber-containing product of the present invention produced as mentioned above has a treatment, improvement or prevention effect on an inflammatory bowel disease, for example, ulcerative colitis. The term "treatment for ulcerative colitis" or "treat ulcerative colitis" as used herein refers to at least one of recovering a diarrhea-state score up to 0 to 1 and recovering a colic histological score up to 0 to 1 by intake or administration of the insoluble dietary fiber-containing product of the present invention. The term "improvement of ulcerative colitis" or "improve ulcerative colitis" as used herein refers to at least one of reducing a diarrhea-state score and reducing a colic histological score by intake or administration of the insoluble dietary fiber-containing product of the present invention. The term "prevention of ulcerative colitis" or "prevent ulcerative colitis" as used herein refers to at least one of maintaining a diarrhea-state score at 0 to 1 and maintaining a colic histological score at 0 to 1 by intake or administration of the insoluble dietary fiber-containing product of the present invention. Note the score of diarrhea state and the colic histological score are defined in Examples as described below.

Accordingly, severe diarrhea caused by an inflammatory bowel disease (for example, ulcerative colitis) can be overcome by orally taking the insoluble dietary fiber-containing product of the present invention. In this manner, the inflammation in the intestinal tract can be improved. Furthermore, onset of an inflammatory bowel disease can be prevented by daily intake thereof. For this purpose, dose of the insoluble dietary fiber-containing product of the present invention per day is preferably 1 g or more, preferably 5 g or more. The insoluble dietary fiber-containing product of the present invention is a component obtained by treating grain plant seeds with a food enzyme and therefore can be taken to daily dietary life. Furthermore, timing of administration or intake may be any time of before meal, during meal or after meal.

The insoluble dietary fiber-containing product of the present invention can be provided by incorporating in a specific composition, for example, a food or drink or a pharmaceutical preparation (or medicament).

When the insoluble dietary fiber-containing product of the present invention is incorporated in a food or drink, this product can be processed into any form of food. Examples of the food or drink, in which the insoluble dietary fiber-containing product of the present invention can be incorporated, include foods or drinks including natural products and processed foods thereof. Furthermore, the insoluble dietary fiber-containing product of the present invention can be contained in an amount of 1 g or more relative to 10 g of a food or drink.

Examples of the food or drink include, but not limited to, functional foods such as a tablet food, a powder food, a granular food, a capsule food and a jelly food, processed products of cereal such as a bread, confectionary, cookie and biscuit, milk products such as milk, yogurt and ice cream, beverages such as a carbonated drink, a soft drink, a fruit juice-containing beverage and a medicinal drink, prepared foods and processed foods.

When the insoluble dietary fiber-containing product of the present invention is incorporated in a pharmaceutical preparation, this product can be formulated into a medicament for the treatment, improvement or prevention of ulcerative colitis. The dosage form of the preparation is not particularly limited. Examples of administration routes include oral and enteral administrations. In the case of oral or enteral administration, the insoluble dietary fiber-containing product of the present invention can be directly administered; however, it can be administered in combination with a pharmaceutically acceptable carrier or excipient and in the form of liquid, suspension, powder, grain, tablet and capsule.

Examples of the pharmaceutically acceptable carrier or excipient may include, but are not limited to, general carriers or excipients including saccharides such as lactose, sucrose and glucose, starch, inorganic materials such as calcium carbonate and calcium sulfate, crystal cellulose, distilled water, purified water, and oils such as sesame oil, soybean oil, corn oil, olive oil, and cotton seed oil. Furthermore, other than the carrier or excipient, additives such as a binder, a lubricant, a dispersant, a suspension, an emulsifier, a diluent, a buffer, anti-oxidizing agent and a bacteria suppresser can be used. The above preparation can be mixed with another pharmaceutical preparation or used in combination. Note that, the preparation may be subjected to a sterilization treatment.

A subject to which the pharmaceutical preparation (or medicament) of the present invention is to be applied is not particularly limited and may be any of healthy persons, patients with ulcerative colitis, patients with ulcerative colitis under therapy, and healthy persons who want to prevent onset of ulcerative colitis, for example. The subject to be administered is not limited to humans and may be animals other than the humans.

The dosage of the pharmaceutical preparation of the present invention varies depending upon various factors such as age, weight, sex, and degree of obesity of subjects; however, the dose of the insoluble food-containing product of the present invention per day is generally 1 g or more, preferably 5 g or more. The interval of administration is not particularly limited.

The insoluble dietary fiber-containing product of the present invention can efficiently improve an inflammatory bowel disease. In addition, since it is a component obtained from grain plant seeds by treatment with a food enzyme, the insoluble dietary fiber-containing product is highly safe and so can usefully be used in a food or drink or a pharmaceutical preparation. In connection with this, since the content of dietary fiber is high, the insoluble dietary fiber-containing product of the present invention advantageously has an effect of improving an inflammatory bowel disease in a relatively small amount.

Furthermore, the insoluble dietary fiber-containing product of the present invention can be produced from a relatively inexpensive material such as rice bran and wheat bran. Thus, it is excellent in view of cost performance.

In the case where the insoluble dietary fiber-containing product of the present invention is contained in a food or drink or a pharmaceutical composition, it can be detected by the following method. To describe more specifically, first, the food or drink or pharmaceutical composition is suspended in water and thereafter sieved in water by use of a 200 mesh (ASTM standard, sieve opening: 0.075 mm) sieve and an insoluble fraction is recovered. Then, the insoluble fraction is stained with by Nile blue or another staining reagent suitable for staining a hydrophobic material and observed by e.g., a fluorescent microscope, thereby detecting the insoluble dietary fiber-containing product of the present invention. At this time, the insoluble dietary fiber-containing product of the present invention can be distinguished from other insoluble compositions by the feature that the insoluble dietary fiber-containing product of the present invention has a layer that can be stained and a layer that cannot be stained are stacked. Examples of other reagents suitable for staining include Sudan III, Sudan black, oil red and fluoro yellow 088.

EXAMPLES

The present invention will be more specifically described by way of the examples below. However, the scope of the invention is not limited by these examples. In the examples, unless otherwise specified, expression of % is based on weight. Furthermore, the analytical values of components were obtained as follows. A crude protein was measured by the Kjeldahl method (the protein conversion coefficient of nitrogen was set to 6.25) and crude lipid was measured by Soxhlet extraction using diethyl ether as an extraction solvent. The content of a dietary fiber was obtained based on the AOAC method.

Preparation Example 1

Brewer's Grains→Roll Mill

Wet-state brewer's grains (water content: 77.6 wt %) were subjected to a press-peeling treatment using a roll mill (roll rotation number: 100 rpm, interval between rolls: 0.08 mm), and thereafter, sieved in water using a 16 mesh sieve (ASTM standard, sieve opening: 1.18 mm). The fraction passed was further sieved using a 50 mesh (ASTM standard, sieve opening: 0.300 mm) sieve. The fraction that did not pass was recovered and subjected to lyophilization to obtain an insoluble dietary fiber-containing product. This was designated as Preparation Sample 1. The analysis values are shown in Table 1 below. Furthermore, a scanning electron micrographic image of the aleurone layer portion contained in Preparation Sample 1 is shown in FIG. 1.

Preparation Example 2

Brewer's Grains→Roll Mill+Hemicellulase)

Figure 2:
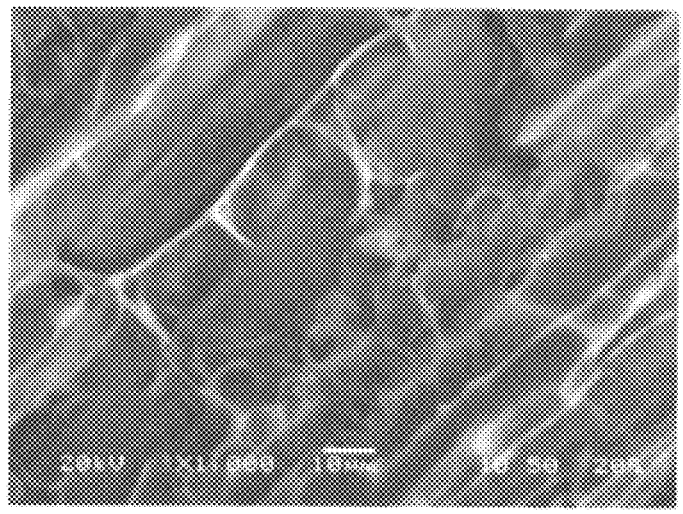
FIG. 2 shows the photograph of an aleurone layer portion contained in Preparation Sample 2.

Wet-state brewer's grains (water content: 77.6 wt %) were subjected to a press-peeling treatment using a roll mill (roll rotation number: 100 rpm, interval between rolls: 0.08 mm), and thereafter, sieved in water using a 16 mesh sieve (ASTM standard, sieve opening: 1.18 mm). The fraction passed was further sieved using a 50 mesh (ASTM standard, sieve opening: 0.300 mm) sieve. The fraction that did not pass was recovered. The fraction recovered was reacted with a 1.0% hemicellulase preparation (Sumiteam NX, manufactured by Shinnihon Chemicals Corporation) in a 50 mM acetate buffer (pH 4.5, 50° C.) overnight. After the aleurone layer of the plant tissue was completely decomposed, sieving was performed in water using a 200 mesh (sieve opening: 0.075 mm) sieve. The fraction that did not pass was recovered and subjected to lyophilization to obtain an insoluble dietary fiber-containing product. This was designated as Preparation Sample 2. The analysis values are shown in Table 1 below. Furthermore, a scanning electron micrographic image of the aleurone layer portion contained in Preparation Sample 2 is shown in FIG. 2.

TABLE 1

The contents of crude proteins and dietary fiber in Preparation Samples 1 and 2 (wt %)

|  | Preparation Sample 1 | Preparation Sample 2 |
| --- | --- | --- |
| Crude proteins | 27.1 | 11.9 |
| Dietary fiber | 60.1 | 77.6 |

Test Example 1

An experiment was performed using the insoluble dietary fiber-containing products obtained in Preparation Examples 1 and 2 as to whether severe diarrhea and abnormality of large-intestinal mucosa caused by ulcerative colitis can be treated or not.

[Material and Method]

As experimental animals, SD male rats (5 weeks old, about 100 g) were preliminarily kept with solid feed (CE-2, manufactured by CLEA Japan, Inc.) for a week and assimilated in an experimentation environment. They were divided into groups of 7 rats and put in use. The feed used in Test Example 1 is as shown in Table 2 below.

Ulcerative colitis was experimentally induced by giving to rats dextran sulfate sodium mixed with a feed. Note that, this method was performed in accordance with the method of Kanauchi et al. (Journal of Gastroenterology 33, 179-188, 1998). The insoluble dietary fiber-containing product was also added to the feed and given. The feed was not forcibly given. After the rats were kept for 5 days, the states of feces and anus were observed. The state of diarrhea was scored for its evaluation. Thereafter, the large intestine was excised out and a part thereof was fixed with a 10% formalin buffer. After that, the mucosa was sectioned in order to take and observe images of the mucosa, thereby scoring a histological state from the images.

Scoring of the state of diarrhea is to score a state of diarrhea of each rat based on scores previously determined depending upon states of feces and conditions of rats, followed by calculating an average value of determined scores.

Score 0: normal
Score 1: slightly soft
Score 2: considerably soft
Score 3: taking feces is virtually impossible
Score 4: diarrhea and mild sore at anus
Score 5: diarrhea and considerably severe sore at anus Histological scoring of the observed mucosal images is to score a state of mucosa at typical sites from anus side to lower side of the large intestine based on the following set of scores in accordance with the method as described by Kanauchi et al (Journal of Gastroenterology and Hepatology 14, 880-888, 1999), followed by calculating an average value of determined scores.

Score 0: normal crypt
Score 1: enlarged crypt
Score 2: 1/3 of the basal crypt is deleted
Score 3: 2/3 of the basal crypt is deleted
Score 4: Entire basal crypt is deleted but epithelial tissue is normal
Score 5: Entire crypt and epithelial tissue are deleted The basic feed contains protein (casein) 14.6%, lipid (corn oil) 5.0%, vitamins 1.0%, minerals 3.5%, and choline chloride 0.2%. The weight is adjusted by use of cornstarch.

TABLE 2

Table of feed composition (wt %)

|  | Comparative Group 1 | Comparative Group 2 | Experimental Group 1 | Experimental Group 2 |
| --- | --- | --- | --- | --- |
| Casein | 14.6 | 10.0 | 13.2 | 12.8 |
| Vitamin mix[*1] | 1.0 | 1.0 | 1.0 | 1.0 |
| Mineral mix[*2] | 3.5 | 3.5 | 3.5 | 3.5 |
| Choline chloride | 0.2 | 0.2 | 0.2 | 0.2 |
| Cellulose | 3.0 | 0 | 0 | 0 |
| Preparation Sample | 0 | 0 | 5.0 | 3.9 |
| GBF | 0 | 10.0 | 0 | 0 |
| Dextran sulfate sodium | 3.0 | 3.0 | 3.0 | 3.0 |
| Corn oil | 5.0 | 5.0 | 5.0 | 5.0 |
| Cornstarch | 69.7 | 67.3 | 69.1 | 70.6 |

[*1]based on AIN-93
[*2]based on AIN-93

Testing Groups were set as follows:

Comparative Group 1: To the basic feed, cellulose (3.0%) was added, and dextran sulfate sodium (3.0%) was added in order to induce ulcerative colitis.

Comparative Group 2: To the basic feed, GBF (germinated barley food, Kirin Yakult Next Stage) 10% was added, casein was added so as to adjust the protein content to 14.6%, and dextran sulfate sodium 3.0% was added in order to induce ulcerative colitis.

Experimental Group 1: To the basic feed, Preparation Sample 1 was added to give a dietary fiber content of 3.0%, casein was added to adjust the protein content to 14.6%, and dextran sulfate sodium 3.0% was added in order to induce ulcerative colitis.

Experimental Group 2: To the basic feed, Preparation Sample 2 was added to give a dietary fiber content of 3.0%, casein was added to adjust the protein content to 14.6%, and dextran sulfate sodium 3.0% was added in order to induce ulcerative colitis.

Results of Test Example 1

Figure 3:
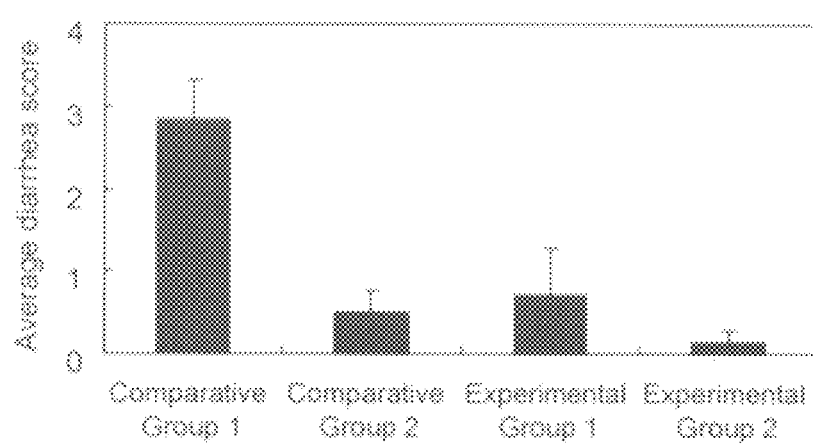
FIG. 3 shows diarrhea scores of Experimental Groups 1 and 2 and Comparative Groups 1 and 2.
Figure 4:
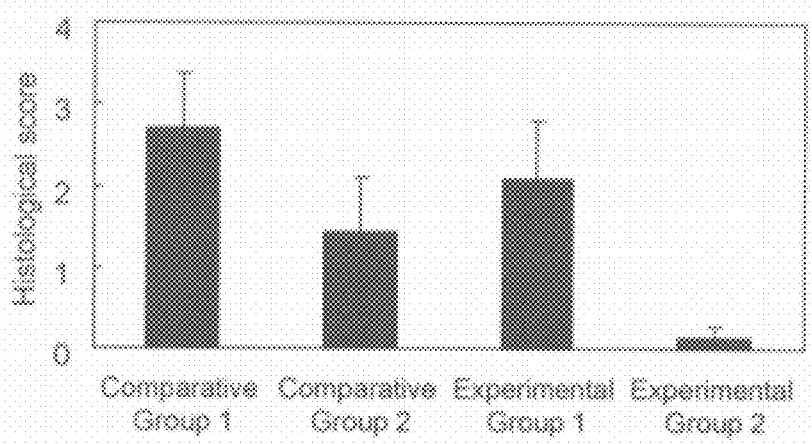
FIG. 4 shows histological scores of Experimental Group 1 and 2 and Comparative Group 1 and 2.

The results are shown in FIG. 3 and FIG. 4. FIG. 3 shows the diarrhea scores of Experimental Groups 1, 2 and Comparative Groups 1, 2. FIG. 4 shows the histological scores of Experimental Groups 1, 2 and Comparative Groups 1, 2. In FIG. 3, diarrhea score improvement effect was observed in Comparative Group 2, Experimental Group 1 and Experimental Group 2. From this, it was confirmed that GBF, Preparation Sample 1 and Preparation Sample 2 have a diarrhea score improvement effect. Furthermore, since the feed was prepared so as to contain a dietary fiber as high as 3.0% in Preparation Sample 1 and Preparation Sample 2, it was found that the effect is exerted in an amount of not more than half of GBF content (10%). When Experimental Group 1 is compared to Experimental Group 2, it was confirmed that Preparation Sample 2, in which the aleurone layer was removed by decomposition with hemicellulase, had a further strong effect. Also from the histological scores of FIG. 4, it was confirmed that the large intestine mucosa was prevented from damage. From these results, it was found that, even if the insoluble dietary fiber-containing product of Preparation Sample 1 or Preparation Sample 2 was taken simultaneously with the ulcerative colitis inducing agent, the condition by the disease was effectively improved.

Preparation Example 3

Naked Malt→Starch Decomposition

Figure 5:
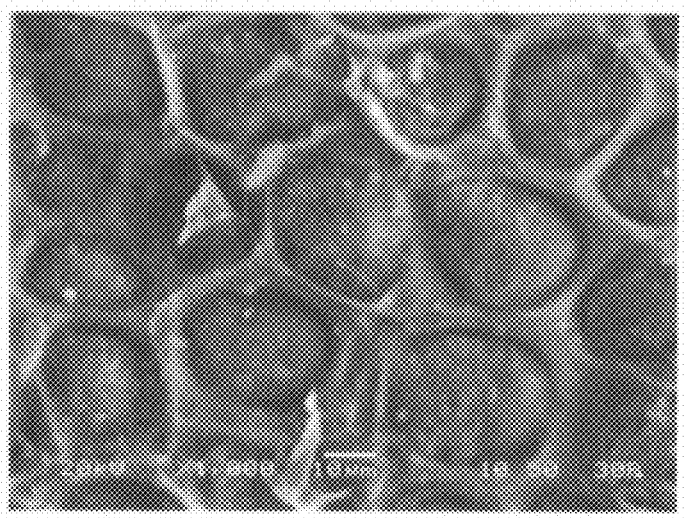
FIG. 5 shows the photograph of an aleurone layer portion contained in Preparation Sample 3.
Figure 6:
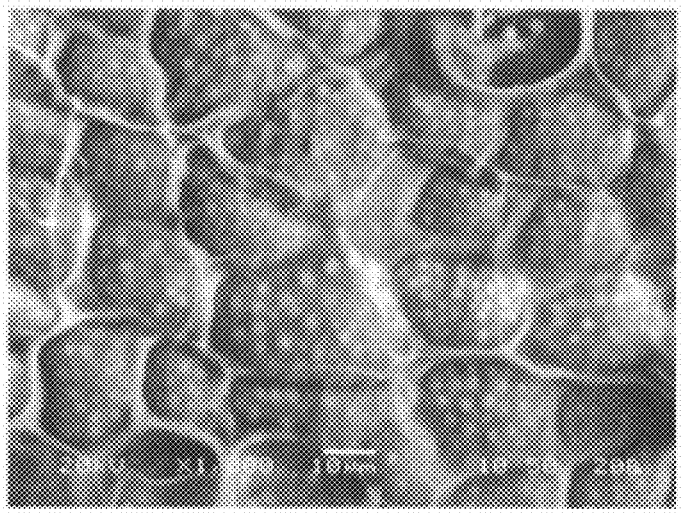
FIG. 6 shows the photograph of an aleurone layer portion in the case that only starch was removed by cold water without applying amylase at 65° C. in Preparation Example 3.

Germinated naked barley (naked malt) was used as a raw material. The husk was removed by a test rice mill TDB2A (rotation number used: 500 rpm) for brewing manufactured by SATAKE Co., Ltd., and thereafter pulverized by a disk mill. Thereafter, water was added and the mixture was maintained at 65° C. for 3 hours to decompose starch with an amylase contained in the naked malt. After starch was decomposed, sieving was performed in water using a 12 mesh sieve (ASTM standard, sieve opening: 1.68 mm). The fraction passed was further sieved using a 200 mesh (ASTM standard, sieve opening: 0.075 mm) sieve. The fraction that did not pass was recovered and subjected to lyophilization to obtain an insoluble dietary fiber-containing product. This was designated as Preparation Sample 3. The analysis values are shown in Table 3 below. Furthermore, a scanning electron micrographic image of the aleurone layer portion contained in Preparation Sample 3 is shown in FIG. 5. Note that, when starch alone was removed with cold water without reacting with an amylase at 65° C., the aleurone layer exhibits the state as shown in FIG. 6.

Preparation Example 4

Naked Malt→Starch Decomposition+Roll Mill+Hemicellulase)

Figure 7:
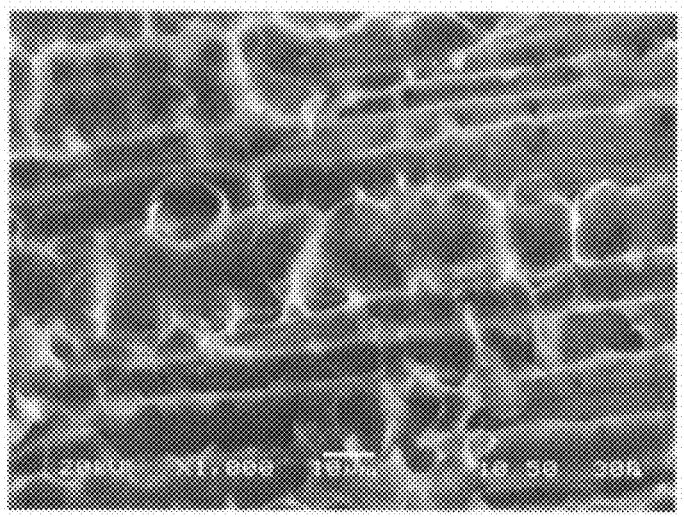
FIG. 7 shows the photograph of an aleurone layer portion contained in Preparation Sample 4.

Germinated naked barley (naked malt) was used as a raw material. The husk was removed by a test rice mill TDB2A (rotation number used: 500 rpm) for brewing manufactured by SATAKE Co., Ltd., and then, pulverized by a disk mill. Thereafter, water was added and the mixture was maintained at 65° C. for 3 hours to decompose starch with an amylase contained in the naked malt. After starch was decomposed, sieving was performed in water using a 12 mesh sieve (ASTM standard, sieve opening: 1.68 mm). The fraction passed was further sieved using a 200 mesh (ASTM standard, sieve opening: 0.075 mm) sieve. The fraction that did not pass was recovered. Next, the fraction recovered in a wet state was subjected to a press-peeling treatment by a roll mill (roll rotation number: 100 rpm, interval between rolls: 0.08 mm) and then sieved in water by use of a 200 mesh (ASTM standard, sieve opening: 0.075 mm) sieve. The fraction that did not pass was recovered and reacted with a 1.0% hemicellulase preparation (Sumiteam NX manufactured by Shinnihon Chemicals Corporation) in a 50 mM acetate buffer (pH 4.5, 50° C.) overnight to completely decompose the aleurone layer of the plant tissue. Again, sieving was performed in water using a 200 mesh (ASTM standard, sieve opening: 0.075 mm) sieve. The fraction that did not pass was recovered and subjected to lyophilization to obtain an insoluble dietary fiber-containing product. This was designated as Preparation Sample 4. The analysis values are shown in Table 3. Furthermore, the scanning electron micrographic image of the aleurone layer portion contained in Preparation Sample 4 is shown in FIG. 7.

TABLE 3

The contents of crude proteins and dietary fiber in Preparation Samples 3 and 4 (wt %)

|  | Preparation Sample 3 | Preparation Sample 4 |
|---|---|---|
| Crude proteins | 15.9 | 8.3 |
| Dietary fiber | 66.0 | 74.2 |

Test Example 2

An experiment was performed using the insoluble dietary fiber-containing products obtained in Preparation Examples 3 and 4 as to whether severe diarrhea and abnormality of large-intestinal mucosa caused by ulcerative colitis can be treated or not.

Material and Method

The test animal and method for inducing ulcerative colitis were the same as those described in Test Example 1, provided that the feed used in Test Example 2 was as shown in Table 4.

The basic feed contains protein (casein) 14.6%, lipid (corn oil) 5.0%, vitamins 1.0%, minerals 3.5% and, choline chloride 0.2%. The weight is adjusted by use of cornstarch.

TABLE 4

Table of feed composition (wt %)

|  | Comparative Group 3 | Comparative Group 4 | Experimental Group 3 | Experimental Group 4 |
|---|---|---|---|---|
| Casein | 14.6 | 10.0 | 13.9 | 14.3 |
| Vitamin mix[*1] | 1.0 | 1.0 | 1.0 | 1.0 |
| Mineral mix[*2] | 3.5 | 3.5 | 3.5 | 3.5 |
| Choline chloride | 0.2 | 0.2 | 0.2 | 0.2 |
| Cellulose | 3.0 | 0 | 0 | 0 |
| Preparation Sample | 0 | 0 | 4.5 | 4.0 |
| GBF | 0 | 10.0 | 0 | 0 |
| Dextran sulfate sodium | 3.0 | 3.0 | 3.0 | 3.0 |
| Corn oil | 5.0 | 5.0 | 5.0 | 5.0 |
| Cornstarch | 69.7 | 67.3 | 68.9 | 69.0 |

[*1]based on AIN-93
[*2]based on AIN-93

Testing Groups were set as follows:

Comparative Group 3: To the basic feed, cellulose (3.0%) was added and dextran sulfate sodium (3.0%) was added in order to induce ulcerative colitis.

Comparative Group 4: To the basic feed, GBF (germinated barley food, Kirin Yakult Next Stage) 10% was added, casein was added so as to adjust the protein content to 14.6%, and dextran sulfate sodium 3.0% was added in order to induce ulcerative colitis.

Experimental Group 3: To the basic feed, Preparation Sample 3 was added to give a dietary fiber content of 3.0%, casein was added to adjust the protein content to 14.6%, and dextran sulfate sodium 3.0% was added in order to induce ulcerative colitis.

Experimental Group 4: To the basic feed, Preparation Sample 4 was added to give a dietary fiber content of 3.0%, casein was added to adjust the protein content to 14.6%, and dextran sulfate sodium 3.0% was added in order to induce ulcerative colitis.

Results of Test Example 2

Figure 8:
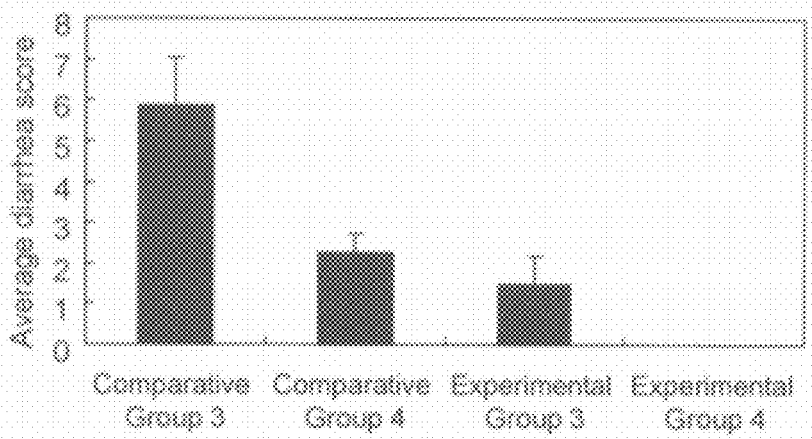
FIG. 8 shows diarrhea scores of Experimental Groups 3 and 4 and Comparative Groups 3 and 4.

The results are shown in FIG. 8. FIG. 8 shows the diarrhea scores of Experimental Groups 3, 4 and Comparative Groups 3, 4. In FIG. 8, the diarrhea score improvement effects of Comparative Group 4, Experimental Group 3 and Experimental Group 4 were confirmed. From this, it was confirmed that GBF, Preparation Sample 3 and Preparation Sample 4 have a diarrhea score improvement effect. Furthermore, since Preparation Sample 3 and Preparation Sample 4 were prepared so as to have as high a dietary fiber content as 3.0%, it was found that the effect was exerted in an amount of not more than half of the GBF content (10%). When Experimental Group 3 was compared to Experimental Group 4, Preparation Sample 4, in which the aleurone layer was removed by decomposition with a roll mill treatment followed by a hemicellulase treatment, had a further stronger diarrhea score improvement effect. From these results, it was found that, even if the insoluble dietary fiber-containing product of Preparation Sample 3 or Preparation Sample 4 was taken simultaneously with an ulcerative colitis inducing agent, the condition by the disease was effectively improved.

Preparation Example 5

Naked Barley→Starch Decomposition

Figure 9:
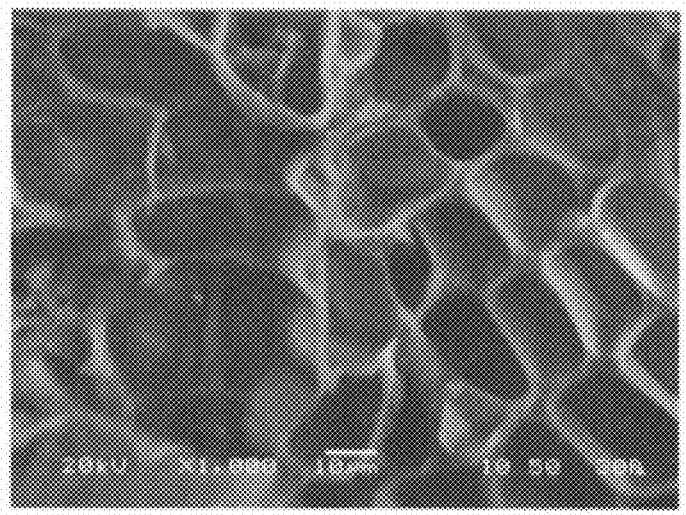
FIG. 9 shows the photograph of an aleurone layer portion contained in Preparation Sample 5.

Ungerminated naked barley (naked barley) was used as a raw material. The husk was removed by a test rice mill TDB2A (rotation number used: 800 rpm) for brewing manufactured by SATAKE Co., Ltd., and thereafter pulverized by a disk mill. Thereafter, a 2.0% amylase preparation (Sumiteam AS manufactured by Shinnihon Chemicals Corporation) was reacted in a 50 mM acetate buffer (pH 4.5, 65° C.) for 3 hours to decompose starch in the naked barley. After starch was decomposed, sieving was performed in water using a 12 mesh sieve (ASTM standard, sieve opening: 1.68 mm). The fraction passed was further sieved using a 200 mesh sieve (ASTM standard, sieve opening: 0.075 mm). The fraction that did not pass was recovered and subjected to lyophilization to obtain an insoluble dietary fiber-containing product. This was designated as Preparation Sample 5. The analysis values are shown in Table 5 below. Furthermore, a scanning electron micrographic image of the aleurone layer portion contained in Preparation Sample 5 is shown in FIG. 9.

Preparation Example 6

Naked Barley→Starch Decomposition+Roll Mill+Hemicellulase)

Figure 10:
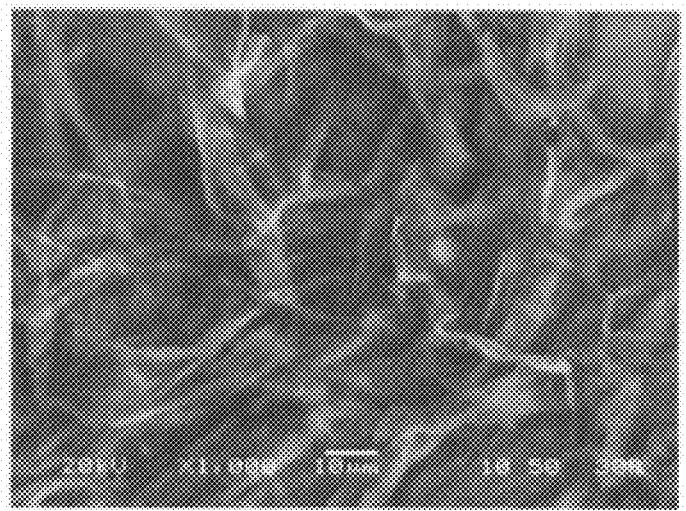
FIG. 10 shows the photograph of an aleurone layer portion contained in Preparation Sample 6.

Ungerminated naked barley (naked barley) was used as a raw material. The husk was removed by a test rice mill TDB2A (rotation number used: 800 rpm) for brewing manufactured by SATAKE Co., Ltd., and thereafter pulverized by a disk mill. Thereafter, a 2.0% amylase preparation (Sumiteam AS manufactured by Shinnihon Chemicals Corporation) was reacted in a 50 mM acetate buffer (pH 4.5, 65° C.) for 3 hours to decompose starch in the naked barley. After starch was decomposed, sieving was performed in water using a 12 mesh sieve (ASTM standard, sieve opening: 1.68 mm). The fraction passed was further sieved using a 200 mesh (ASTM standard, sieve opening: 0.075 mm) sieve. The fraction that did not pass was recovered. The fraction recovered in a wet state was subjected to a press-peeling treatment using a roll mill (roll rotation number: 100 rpm, interval between rolls: 0.08 mm) and then sieved in water by use of a 200 mesh (ASTM standard, sieve opening: 0.075 mm) sieve. The fraction that did not pass was recovered. Next, the fraction recovered was reacted with a 1.0% hemicellulase preparation (Sumiteam NX manufactured by Shinnihon Chemicals Corporation) in a 50 mM acetate buffer (pH 4.5, 50° C.) overnight to completely decompose the aleurone layer of the plant tissue. Again, sieving was performed in water using a 200 mesh (ASTM standard, sieve opening: 0.075 mm) sieve. The fraction that did not pass was recovered and subjected to lyophilization to obtain an insoluble dietary fiber-containing product. This was designated as Preparation Sample 6. The analysis values are shown in Table 5. Furthermore, a scanning electron micrographic image of the aleurone layer portion contained in Preparation Sample 6 is shown in FIG. 10.

TABLE 5

The contents of crude proteins and dietary fiber in Preparation Samples 5 and 6 (wt %)

|  | Preparation Sample 5 | Preparation Sample 6 |
| --- | --- | --- |
| Crude proteins | 26.5 | 8.3 |
| Dietary fiber | 60.6 | 77.8 |

Test Example 3

An experiment was performed using the insoluble dietary fiber-containing products obtained in Preparation Examples 5, 6 as to whether severe diarrhea and abnormality of large-intestinal mucosa caused by ulcerative colitis can be treated or not.

Material and Method

Following Test Example 1, The test animal and method for inducing ulcerative colitis were the same as those described in Test Example 1, provided that the feed used in Test Example 3 was as shown in Table 6.

The basic feed contains protein (casein) 14.6%, lipid (corn oil) 5.0%, vitamins 1.0%, minerals 3.5%, and choline chloride 0.2%. The weight is adjusted by use of cornstarch.

TABLE 6

Table of feed composition (wt %)

|  | Comparative Group 5 | Comparative Group 6 | Experimental Group 5 | Experimental Group 6 |
| --- | --- | --- | --- | --- |
| Casein | 14.6 | 10.0 | 13.3 | 14.3 |
| Vitamin mix*[1] | 1.0 | 1.0 | 1.0 | 1.0 |
| Mineral mix*[2] | 3.5 | 3.5 | 3.5 | 3.5 |
| Choline chloride | 0.2 | 0.2 | 0.2 | 0.2 |
| Cellulose | 3.0 | 0 | 0 | 0 |
| Preparation Sample | 0 | 0 | 4.9 | 3.9 |
| GBF | 0 | 10.0 | 0 | 0 |
| Dextran sulfate sodium | 3.0 | 3.0 | 3.0 | 3.0 |
| Corn oil | 5.0 | 5.0 | 5.0 | 5.0 |
| Cornstarch | 69.7 | 67.3 | 69.1 | 69.2 |

*[1]based on AIN-93
*[2]based on AIN-93

Testing Groups were set as follows:

Comparative Group 5: To the basic feed, cellulose (3.0%) was added and dextran sulfate sodium (3.0%) was added in order to induce ulcerative colitis.

Comparative Group 6: To the basic feed, GBF (germinated barley food, Kirin Yakult Next Stage) 10% was added, casein was added so as to adjust the protein content to 14.6%, and dextran sulfate sodium 3.0% was added in order to induce ulcerative colitis.

Experimental Group 5: To the basic feed, Preparation Sample 5 was added to give a dietary fiber content of 3.0%, casein was added so as to adjust the protein content to 14.6%, and dextran sulfate sodium 3.0% was added in order to induce ulcerative colitis.

Experimental Group 6: To the basic feed, Preparation Sample 6 was added to give a dietary fiber content of 3.0%, casein was added so as to adjust the protein content to 14.6%, and dextran sulfate sodium 3.0% was added in order to induce ulcerative colitis.

Results of Test Example 3

Figure 11:
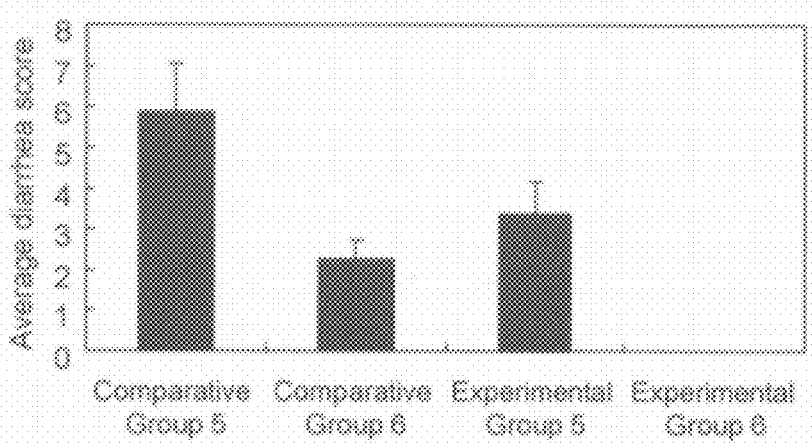
FIG. 11 shows diarrhea scores of Experimental Groups 5 and 6 and Comparative Groups 5 and 6.

The results are shown in FIG. 11. FIG. 11 shows the diarrhea scores of Experimental Groups 5, 6 and Comparative Groups 5, 6. In FIG. 11, the diarrhea score improvement effects of Comparative Group 6, Experimental Group 5 and Experimental Group 6 were confirmed. From this, it was confirmed that GBF, Preparation Sample 5 and Preparation Sample 6 hada diarrhea score improvement effect. Furthermore, since feed was prepared so as to have as high a dietary fiber content as 3.0% in Preparation Sample 5 and Preparation Sample 6, it was found that the effect was exerted in an amount of not more than half of the GBF content (10%). When Experimental Group 5 was compared to Experimental Group 6, Preparation Sample 6, in which the aleurone layer was removed by decomposition with a roll-mill treatment followed by a hemicellulase treatment, had a further stronger diarrhea score improvement effect. From these results, it was found that, even if the insoluble dietary fiber-containing product of Preparation Sample 5 or Preparation Sample 6 was taken simultaneously with an ulcerative colitis inducing agent, the condition by the disease is effectively improved. Further, it was found that, even if ungerminated seeds were used, ungerminated seed-derived dietary fiber-containing product also had a diarrhea score improvement effect and an anti-inflammatory activity by performing a roll mill treatment in combination with a hemicellulase treatment.

Preparation Example 7

Naked Malt→Starch Decomposition+Roll Mill

Germinated naked barley (naked malt) was used as a raw material. The husk was removed by using a test rice mill TDB2A (rotation number used: 500 rpm) for brewing manufactured by SATAKE Co., Ltd., and thereafter pulverized by a disk mill. Thereafter, water was added and the mixture was maintained at 65° C. for 3 hours to decompose starch with an amylase contained in the naked malt. After starch was decomposed, sieving was performed in water using a 12 mesh sieve (ASTM standard, sieve opening: 1.68 mm). The fraction passed was further sieved using a 200 mesh (ASTM standard, sieve opening: 0.075 mm) sieve. The fraction that did not pass was recovered. Next, the fraction recovered in a wet state was subjected to a press-peeling treatment using a roll mill (roll rotation number: 100 rpm, interval between rolls: 0.08 mm) and then sieved in water by use of a 200 mesh (ASTM standard, sieve opening: 0.075 mm) sieve. The fraction that did not pass was recovered and subjected to lyophilization to obtain an insoluble dietary fiber-containing product. This was designated as Preparation Sample 7. The analysis values are shown in Table 7 below.

Preparation Example 8

Naked Malt→Starch Decomposition+Hemicellulase

Germinated naked barley (naked malt) was used as a raw material. The husk was removed by using a test rice mill TDB2A (rotation number used: 500 rpm) for brewing manufactured by SATAKE Co., Ltd., and thereafter pulverized by using a disk mill. Thereafter, water was added and the mixture was maintained at 65° C. for 3 hours to decompose starch with an amylase contained in the naked malt. After starch was decomposed, a 1.0% hemicellulase preparation (Sumiteam NX manufactured by Shinnihon Chemicals Corporation) was reacted in a 50 mM acetate buffer (pH 4.5, 50° C.) overnight to completely decompose the aleurone layer of the plant tissue and then sieved using a 200 mesh (ASTM standard, sieve opening: 0.075 mm) sieve. The fraction that did not pass was recovered and subjected to lyophilization to obtain an insoluble dietary fiber-containing product. This was designated as Preparation Sample 8. The analysis values are shown in Table 7 below.

Preparation Example 9

Naked Malt→Starch Decomposition+Roll Mill+Hemicellulase)

The same treatment as in Preparation Example 4 was repeated to obtain an insoluble dietary fiber-containing product. This was designated as Preparation Sample 9. The analysis values are shown in Table 7.

TABLE 7

| The contents of crude proteins and dietary fiber in Preparation Samples 7, 8 and 9 (wt %) | | | |
|---|---|---|---|
| | Preparation Sample 7 | Preparation Sample 8 | Preparation Sample 9 |
| Crude proteins | 12.2 | 9.6 | 8.1 |
| Dietary fiber | 71.5 | 71.5 | 72.1 |

Test Example 4

An experiment was performed using the insoluble dietary fiber-containing products obtained in Preparation Examples 7, 8 and 9 as to whether severe diarrhea and abnormality of large-intestinal mucosa caused by ulcerative colitis can be treated or not.

[Material and Method]

The test animal and method for inducing ulcerative colitis were the same as those described in Test Example 1, provided that the feed used in Test Example 4 is as shown in Table 8.

The basic feed contains protein (casein) 14.6%, lipid (corn oil) 5.0%, vitamins 1.0%, minerals 3.5%, and choline chloride 0.2%. The weight is adjusted by use of cornstarch.

TABLE 8

Table of feed composition (wt %)

|  | Comparative Group 7 | Comparative Group 8 | Experimental Group 7 | Experimental Group 8 | Experimental Group 9 |
|---|---|---|---|---|---|
| Casein | 14.6 | 10.0 | 14.1 | 14.2 | 14.3 |
| Vitamin mix*[1] | 1.0 | 1.0 | 1.0 | 1.0 | 1.0 |
| Mineral mix*[2] | 3.5 | 3.5 | 3.5 | 3.5 | 3.5 |
| Choline chloride | 0.2 | 0.2 | 0.2 | 0.2 | 0.2 |
| Cellulose | 3.0 | 0 | 0 | 0 | 0 |
| Preparation Sample | 0 | 0 | 4.2 | 4.2 | 4.2 |
| GBF | 0 | 10.0 | 0 | 0 | 0 |
| Dextran sulfate sodium | 3.0 | 3.0 | 3.0 | 3.0 | 3.0 |
| Corn oil | 5.0 | 5.0 | 5.0 | 5.0 | 5.0 |
| Cornstarch | 69.7 | 67.3 | 69.0 | 68.9 | 68.9 |

*[1]based on AIN-93
*[2]based on AIN-93

Testing Groups were set as follows:

Comparative Group 7: To the basic feed, cellulose (3.0%) was added and dextran sulfate sodium (3.0%) was added in order to induce ulcerative colitis.

Comparative Group 8: To the basic feed, 10% of GBF (germinated barley food, Kirin Yakult Next Stage) was added, casein was added to adjust the protein content to 14.6%, and dextran sulfate sodium 3.0% was added in order to induce ulcerative colitis.

Experimental Group 7: To the basic feed, Preparation Sample 7 was added to give a dietary fiber content of 3.0%, casein was added so as to adjust the protein content to 14.6%, and dextran sulfate sodium 3.0% was added in order to induce ulcerative colitis.

Experimental Group 8: To the basic feed, Preparation Sample 8 was added to give a dietary fiber content of 3.0%, casein was added so as to adjust the protein content to 14.6%, and dextran sulfate sodium 3.0% was added in order to induce ulcerative colitis.

Experimental Group 9: To the basic feed, Preparation Sample 9 was added to give a dietary fiber content of 3.0%, casein was added to adjust the protein content to 14.6%, and dextran sulfate sodium 3.0% was added in order to induce ulcerative colitis.

Results of Test Example 4

Figure 12:
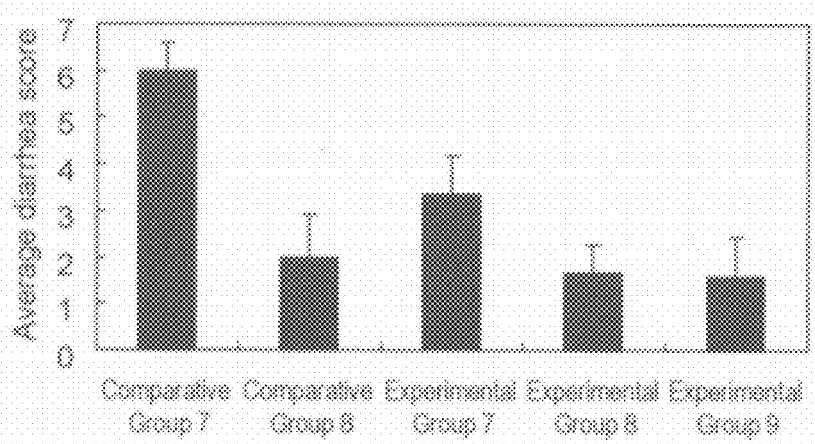
FIG. 12 shows diarrhea scores of Experimental Groups 7, 8 and 9 and Comparative Groups 7 and 8.
Figure 13:
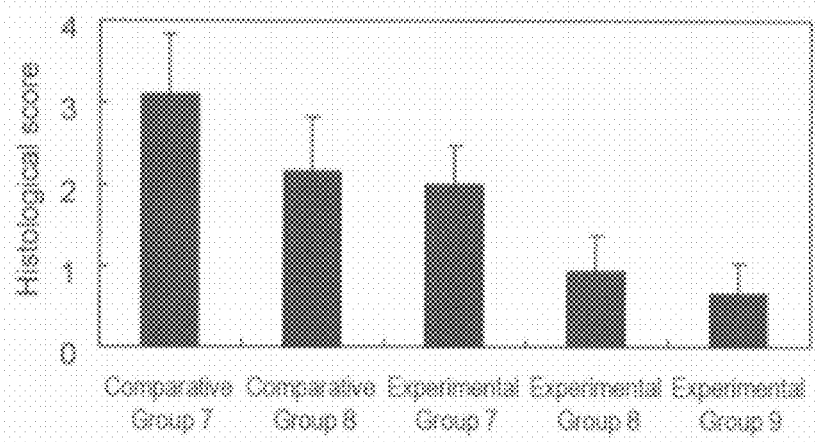
FIG. 13 shows histological scores of Experimental Groups 7, 8 and 9 and Comparative Groups 7 and 8.

The results are shown in FIG. 12 and FIG. 13. FIG. 12 shows the diarrhea scores of Experimental Groups 7, 8, 9 and Comparative Groups 7, 8. FIG. 13 shows the histological scores of Experimental Groups 7, 8, 9 and Comparative Groups 7, 8. In FIG. 12, the diarrhea score improvement effects of Comparative Group 8, Experimental Group 7, Experimental Group 8 and Experimental Group 9 were confirmed. From this, it was confirmed that GBF, Preparation Sample 7, Preparation Sample 8 and Preparation Sample 9 had a diarrhea score improvement effect. Furthermore, since Preparation Sample 7, Preparation Sample 8 and Preparation Sample 9 were prepared so as to have a dietary fiber content as high as 3.0%, it was found that the effect was exerted in an amount of not more than half of the GBF content (10%). When Experimental Group 7, Experimental Group 8 and Experimental Group 9 were compared, it was confirmed that either of Preparation Sample 8, in which the aleurone layer was removed by decomposition with a hemicellulase treatment, and Preparation Sample 9, in which the aleurone layer was removed by decomposition with a roll mill treatment followed by a hemicellulase treatment, had a stronger diarrhea score improvement effect than Preparation Sample 7, in which the aleurone layer was not completely decomposed. Also from the histological score of FIG. 13, it was confirmed that damage of the large intestine mucosa was prevented in Preparation Sample 7, Preparation Sample 8 and Preparation Sample 9. Furthermore, similarly to the diarrhea scores, it was confirmed that either of Preparation Sample 8 or Preparation Sample 9 had a stronger effect than Preparation Sample 7. From these results, it was found that, even if the insoluble dietary fiber-containing product of Preparation Sample 7, Preparation Sample 8 or Preparation Sample 9 was taken simultaneously with an ulcerative colitis inducing agent, the condition by the disease was effectively improved.

Preparation Example 10

Rice Bran→Starch Decomposition+Hemicellulase

Rice bran was used as a raw material. A 2.0% amylase preparation (Sumiteam AS manufactured by Shinnihon Chemicals Corporation) was reacted in a 50 mM acetate buffer (pH 4.5, 65° C.) for 3 hours to decompose starch in the rice bran. After starch was decomposed, sieving was performed in water using a 200 mesh (ASTM standard, sieve opening: 0.075 mm) sieve. The fraction that did not pass was recovered and then reacted with a 1.0% hemicellulase preparation (Sumiteam NX manufactured by Shinnihon Chemicals Corporation) in a 50 mM acetate buffer (pH 4.5, 50° C.) overnight to completely decompose the aleurone layer of the plant tissue. Thereafter, sieving was performed again in water using a 200 mesh (ASTM standard, sieve opening: 0.075 mm) sieve. The fraction that did not pass was recovered and subjected to lyophilization to obtain an insoluble dietary fiber-containing product. This was designated as Preparation Sample 10. The analysis values are shown in Table 9.

TABLE 9

The contents of crude proteins and dietary fiber in Preparation Sample 10 (wt %)

|  | Preparation Sample 10 |
|---|---|
| Crude proteins | 9.8 |
| Dietary fiber | 63.1 |

Test Example 5

An experiment was performed using the insoluble dietary fiber-containing product obtained in Preparation Example 10 as to whether severe diarrhea and abnormality of large-intestinal mucosa caused by ulcerative colitis can be treated or not.

[Material and Method]

Following Test Example 1, The test animal and method for inducing ulcerative colitis were the same as those described in Test Example 1, provided that the feed used in Test Example 5 was as shown in Table 10.

The basic feed contains protein (casein) 14.6%, lipid (corn oil) 5.0%, vitamins 1.0%, minerals 3.5%, and choline chloride 0.2%. The weight is adjusted by use of cornstarch.

TABLE 10

Table of feed composition (wt %)

|  | Comparative Group 9 | Comparative Group 10 | Experimental Group 10 |
|---|---|---|---|
| Casein | 14.6 | 10.0 | 14.1 |
| Vitamin mix[*1] | 1.0 | 1.0 | 1.0 |
| Mineral mix[*2] | 3.5 | 3.5 | 3.5 |
| Choline chloride | 0.2 | 0.2 | 0.2 |
| Cellulose | 3.0 | 0 | 0 |
| Preparation Sample | 0 | 0 | 4.8 |
| GBF | 0 | 10.0 | 0 |
| Dextran sulfate sodium | 3.0 | 3.0 | 3.0 |
| Corn oil | 5.0 | 5.0 | 5.0 |
| Cornstarch | 69.7 | 67.3 | 68.4 |

[*1]based on AIN-93
[*2]based on AIN-93

Testing Groups were set as follows:

Comparative Group 9: To the basic feed, cellulose (3.0%) was added and dextran sulfate sodium (3.0%) was added in order to induce ulcerative colitis.

Comparative Group 10: To the basic feed, GBF (germinated barley food, Kirin Yakult Next Stage) 10% was added, casein was added so as to adjust the protein content to 14.6%, and dextran sulfate sodium 3.0% was added in order to induce ulcerative colitis.

Experimental Group 10: To the basic feed, Preparation Sample 10 was added to give a dietary fiber content of 3.0%, casein was added to adjust the protein content to 14.6%, and dextran sulfate sodium 3.0% was added in order to induce ulcerative colitis.

Results of Test Example 5

Figure 14:
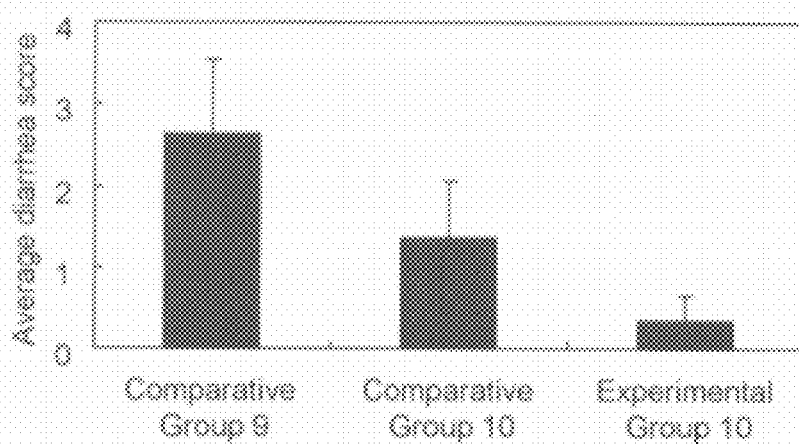
FIG. 14 shows diarrhea scores of Experimental Groups 10 and Comparative Groups 9 and 10.
Figure 15:
FIG. 15 is the photograph showing the state of the large-intestinal mucosa of an organism according to Comparative Group 9.
Figure 16:
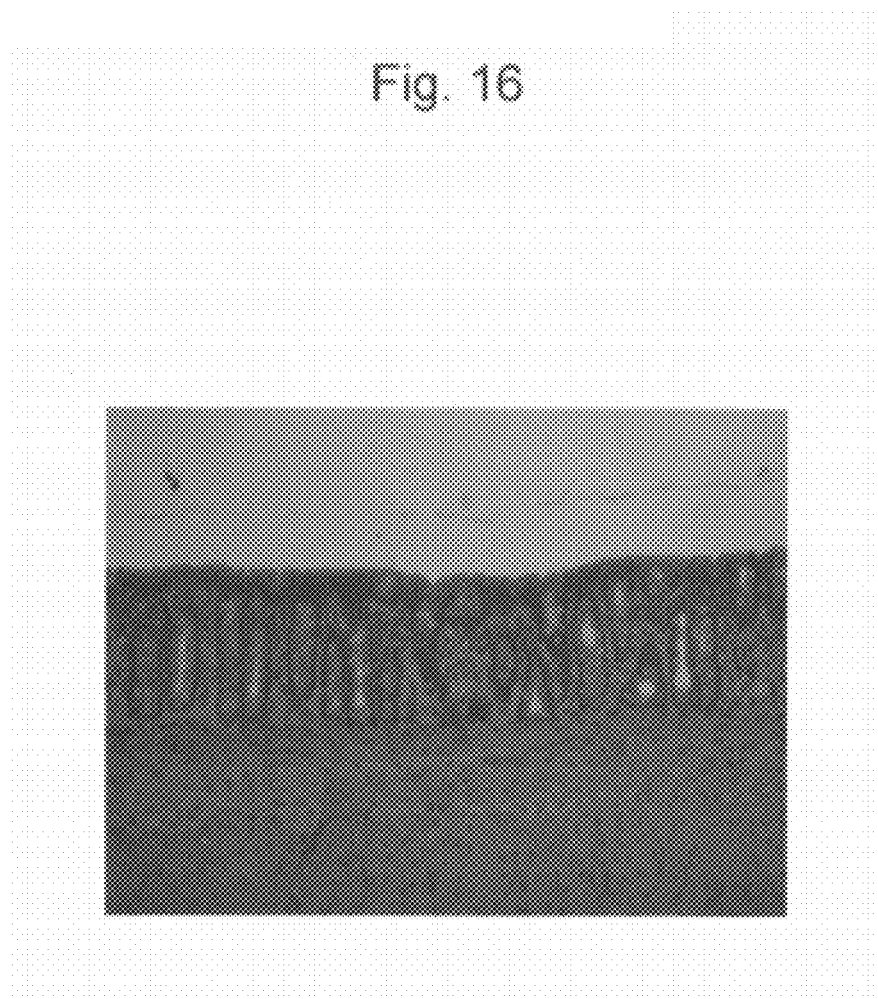
FIG. 16 is the photograph showing the state of the large-intestinal mucosa of a rat in Comparative Group 10.
Figure 17:
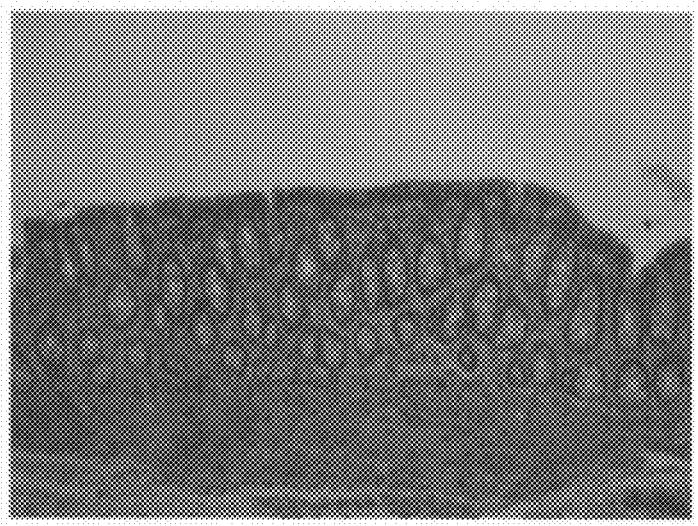
FIG. 17 is the photograph showing the state of the large-intestinal mucosa of a rat in Experimental Group 10.

The results are shown in FIGS. 14 to 17. FIG. 14 shows the diarrhea scores of Experimental Group 10 and Comparative Groups 9, 10. FIG. 15 is a photograph of the large intestine mucosa of an animal of Comparative Group 9. FIG. 16 is a photograph of the large intestine mucosa of an animal of Comparative Group 10. FIG. 17 is a photograph of the large intestine mucosa of an animal of Experimental Group 10. In FIG. 14, the diarrhea score improvement effects of Comparative Group 10 and Experimental Group 10 were confirmed. From this, it was confirmed that GBF and Preparation Sample 10 have a diarrhea score improvement effect. Furthermore, Preparation Sample 10 was prepared so as to have as high a dietary fiber content as 3.0%, it was found that the effect was exerted in an amount of not more than half of the GBF content (10%). Also from the photographs of FIGS. 15 to 17 showing the state of the large intestine mucosa, a normal mucosa image was observed in Comparative Group 10 and Experimental Group 10. From these results, it was found that, even if the insoluble dietary fiber-containing product of Preparation Sample 10 was taken simultaneously with an ulcerative colitis inducing agent, the condition of the disease is effectively improved.

Preparation Example 11

Rice Bran→Starch Decomposition+Hemicellulase

The same treatment as in Preparation Example 10 was repeated to obtain an insoluble dietary fiber-containing product. This was designated as Preparation Sample 11. The analysis values are shown in the following Table 11.

Preparation Example 12

Rice Bran→Starch Decomposition+Hemicellulase→Defatting Treatment

Rice bran was used as a raw material. A 2.0% amylase preparation (Sumiteam AS manufactured by Shinnihon Chemicals Corporation) was reacted in a 50 mM acetate buffer (pH 4.5, 65° C.) for 3 hours to decompose starch in the rice bran. After starch was decomposed, sieving was performed in water using a 200 mesh (ASTM standard, sieve opening: 0.075 mm) sieve. The fraction that did not pass was recovered and then reacted with a 1.0% hemicellulase preparation (Sumiteam NX manufactured by Shinnihon Chemicals Corporation) in a 50 mM acetate buffer (pH 4.5, 50° C.) overnight to completely decompose the aleurone layer of the plant tissue. Thereafter, sieving was performed again in water using a 200 mesh (ASTM standard, sieve opening: 0.075 mm) sieve. The fraction that did not pass was recovered. The fraction recovered was subjected to a defatting treatment with ethanol and then subjected to lyophilization to obtain an insoluble dietary fiber-containing product. This was designated as Preparation Sample 12. The analysis values are shown in the following Table 11.

TABLE 11

The contents of crude proteins and dietary fiber in Preparation Samples 11 and 12 (wt %)

|  | Preparation Sample 11 | Preparation Sample 12 |
|---|---|---|
| Crude proteins | 9.2 | 12.6 |
| Dietary fiber | 66.0 | 78.8 |

Test Example 6

An experiment was performed using the insoluble dietary fiber-containing products obtained in Preparation Examples 11 and 12 as to whether severe diarrhea and abnormality of large-intestinal mucosa caused by ulcerative colitis can be treated or not.

[Material and Method]

The test animal and method for inducing ulcerative colitis were the same as those described in Test Example 1, provided that the feed used in Test Example 6 was as shown in Table 12.

The basic feed contains protein (casein) 14.6%, lipid (corn oil) 5.0%, vitamins 1.0%, minerals 3.5%, and choline chloride 0.2%. The weight is adjusted by use of cornstarch.

TABLE 12

Table of feed composition (wt %)

|  | Comparative Group 11 | Comparative Group 12 | Experimental Group 11 | Experimental Group 12 |
|---|---|---|---|---|
| Casein | 14.6 | 10.0 | 14.2 | 14.1 |
| Vitamin mix[*1] | 1.0 | 1.0 | 1.0 | 1.0 |
| Mineral mix[*2] | 3.5 | 3.5 | 3.5 | 3.5 |
| Choline chloride | 0.2 | 0.2 | 0.2 | 0.2 |
| Cellulose | 3.0 | 0 | 0 | 0 |
| Preparation Sample | 0 | 0 | 4.5 | 3.8 |
| GBF | 0 | 10.0 | 0 | 0 |

TABLE 12-continued

Table of feed composition (wt %)

|  | Comparative Group 11 | Comparative Group 12 | Experimental Group 11 | Experimental Group 12 |
|---|---|---|---|---|
| Dextran sulfate sodium | 3.0 | 3.0 | 3.0 | 3.0 |
| Corn oil | 5.0 | 5.0 | 5.0 | 5.0 |
| Cornstarch | 69.7 | 67.3 | 68.6 | 69.4 |

*[1] based on AIN-93
*[2] based on AIN-93

Testing Groups were set as follows:

Comparative Group 11: To the basic feed, cellulose (3.0%) was added and dextran sulfate sodium (3.0%) was added in order to induce ulcerative colitis.

Comparative Group 12: To the basic feed, GBF (germinated barley food, Kirin Yakult Next Stage) 10% was added, casein was added so as to adjust the protein content to 14.6%, and dextran sulfate sodium 3.0% was added in order to induce ulcerative colitis.

Experimental Group 11: To the basic feed, Preparation Sample 11 was added to give a dietary fiber content of 3.0%, casein was added so as to adjust the protein content to 14.6%, and dextran sulfate sodium 3.0% was added in order to induce ulcerative colitis.

Experimental Group 12: To the basic feed, Preparation Sample 12 was added to give a dietary fiber content of 3.0%, casein was added so as to adjust the protein content to 14.6%, and dextran sulfate sodium 3.0% was added in order to induce ulcerative colitis.

Results of Test Example 6

Figure 18:
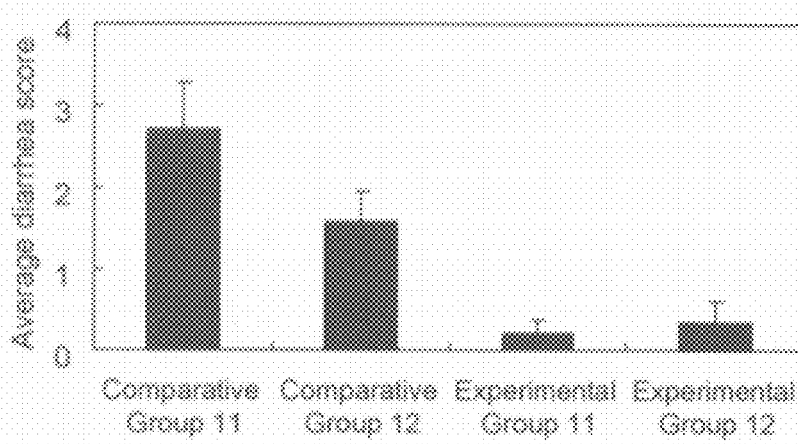
FIG. 18 shows diarrhea scores of Experimental Groups 11 and 12 and Comparative Groups 11 and 12.

The results are shown in FIG. 18. FIG. 18 shows the diarrhea scores of Experimental Groups 11, 12 and Comparative Groups 11, 12. The diarrhea score improvement effect was observed in Experimental Group 11 and Experimental Group 12. From this, it was found that, even if a defatting treatment was performed with ethanol, the diarrhea score improvement effect was not lost.

Preparation Example 13

Bran→Starch Decomposition+Hemicellulase

Bran was used as a raw material. A 2.0% amylase preparation (Sumiteam AS manufactured by Shinnihon Chemicals Corporation) was reacted in a 50 mM acetate buffer (pH 4.5, 65° C.) for 3 hours to decompose starch in the bran. After starch was decomposed, sieving was performed in water using a 200 mesh (ASTM standard, sieve opening: 0.075 mm) sieve. The fraction that did not pass was recovered and then reacted with a 1.0% hemicellulase preparation (Sumiteam NX manufactured by Shinnihon Chemicals Corporation) in a 50 mM acetate buffer (pH 4.5, 50° C.) overnight to completely decompose the aleurone layer of the plant tissue. Thereafter, sieving was performed again in water using a 200 mesh (ASTM standard, sieve opening: 0.075 mm) sieve. The fraction that did not pass was recovered and subjected to lyophilization to obtain an insoluble dietary fiber-containing product. This was designated as Preparation Sample 13. The analysis values are shown in Table 13.

TABLE 13

The contents of crude proteins and dietary fiber in Preparation Sample 13 (wt %)

|  | Preparation Sample 13 |
|---|---|
| Crude proteins | 4.34 |
| Dietary fiber | 88.8 |

Test Example 7

An experiment was performed using the insoluble dietary fiber-containing product obtained in Preparation Example 13 as to whether severe diarrhea and abnormality of large-intestinal mucosa caused by ulcerative colitis can be treated or not.

[Material and Method]

Following Test Example 1, The test animal and method for inducing ulcerative colitis were the same as those described in Test Example, provided that the feed used in Test Example 7 is as shown in Table 14.

The basic feed contains protein (casein) 14.6%, lipid (corn oil) 5.0%, vitamins 1.0%, minerals 3.5%, and choline chloride 0.2%. The weight is adjusted by use of cornstarch.

TABLE 14

Table of feed composition (wt %)

|  | Comparative Group 13 | Comparative Group 14 | Experimental Group 13 |
|---|---|---|---|
| Casein | 14.6 | 10.0 | 14.4 |
| Vitamin mix*[1] | 1.0 | 1.0 | 1.0 |
| Mineral mix*[2] | 3.5 | 3.5 | 3.5 |
| Choline chloride | 0.2 | 0.2 | 0.2 |
| Cellulose | 3.0 | 0 | 0 |
| Preparation Sample | 0 | 0 | 3.4 |
| GBF | 0 | 10.0 | 0 |
| Dextran sulfate sodium | 3.0 | 3.0 | 3.0 |
| Corn oil | 5.0 | 5.0 | 5.0 |
| Cornstarch | 69.7 | 67.3 | 69.5 |

*[1] based on AIN-93
*[2] based on AIN-93

Testing Groups were set as follows:

Comparative Group 13: To the basic feed, cellulose (3.0%) was added and dextran sulfate sodium (3.0%) was added in order to induce ulcerative colitis.

Comparative Group 14: To the basic feed, GBF (germinated barley food, Kirin Yakult Next Stage) 10% was added, casein was added so as to adjust the protein content to 14.6%, and dextran sulfate sodium 3.0% was added in order to induce ulcerative colitis.

Experimental Group 13: To the basic feed, Preparation Sample 13 was added to give a dietary fiber content of 3.0%, casein was added so as to adjust the protein content to 14.6%, and dextran sulfate sodium 3.0% was added in order to induce ulcerative colitis.

Results of Test Example 7

Figure 19:
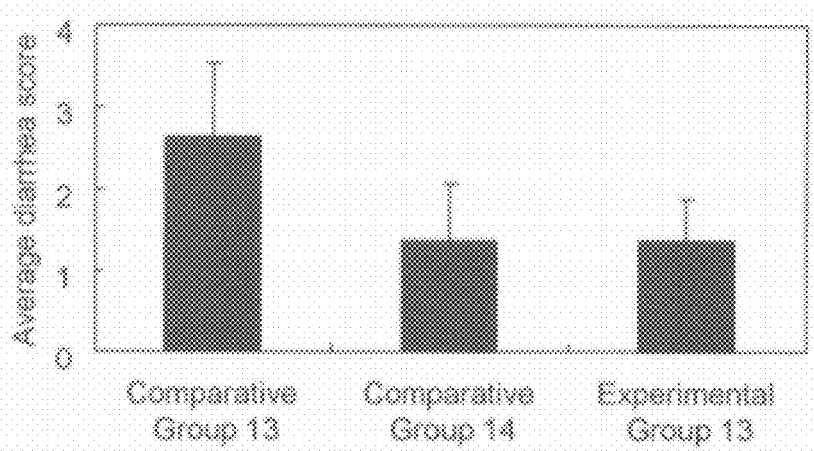
FIG. 19 shows diarrhea scores of Experimental Group 13 and Comparative Groups 13 and 14.

The results are shown in FIG. 19. FIG. 19 shows the diarrhea scores of Experimental Group 13 and Comparative Groups 13, 14. The diarrhea score improvement effect of Experimental Group 13 was confirmed. From this, it was found that, when bran was used as a raw material, a diarrhea score improvement effect was exerted.

Note that, those skilled in the art will easily understand that the materials other than the materials tested in the above Test Examples and derived from seeds of a grain plant within the scope of the invention would exert the same effect.

Preparation Example 14

Rice Bran→Starch Decomposition+Hemicellulase

Figure 20:
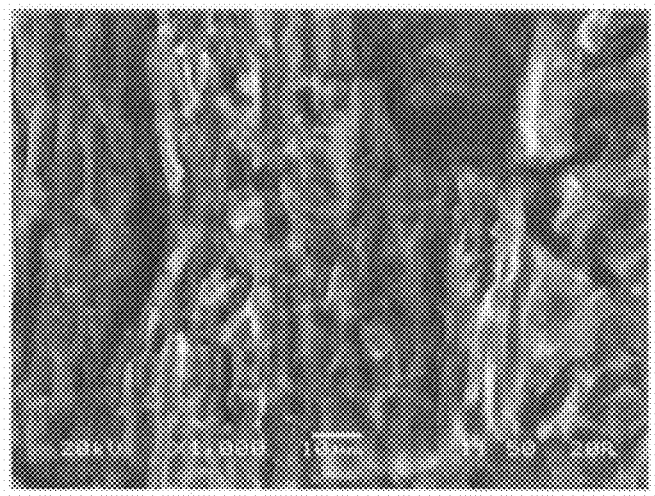
FIG. 20 shows the photograph of an aleurone layer portion of Preparation Sample 14.

Rice bran was used as a raw material. A 2.0% amylase preparation (Sumiteam AS manufactured by Shinnihon Chemicals Corporation) was reacted in a 50 mM acetate buffer (pH 4.5, 65° C.) for 3 hours to decompose starch in the rice bran. After starch was decomposed, sieving was performed in water using a 200 mesh (ASTM standard, sieve opening: 0.075 mm) sieve. The fraction that did not pass was recovered and then reacted with a 1.0% hemicellulase preparation (Sumiteam NX manufactured by Shinnihon Chemicals Corporation) in a 50 mM acetate buffer (pH 4.5, 50° C.) overnight to completely decompose the aleurone layer of the plant tissue. Thereafter, sieving was performed again in water using a 200 mesh (ASTM standard, sieve opening: 0.075 mm) sieve. The fraction that did not pass was recovered and subjected to lyophilization to obtain an insoluble dietary fiber-containing product. This was designated as Preparation Sample 14. The analysis values are shown in Table 15 below. Furthermore, a scanning electron micrographic image of the aleurone layer portion contained in Preparation Sample 14 is shown in FIG. 20.

Preparation Example 15

Rice Bran→Removal of Starch by Homogenously Stirring

Figure 21:
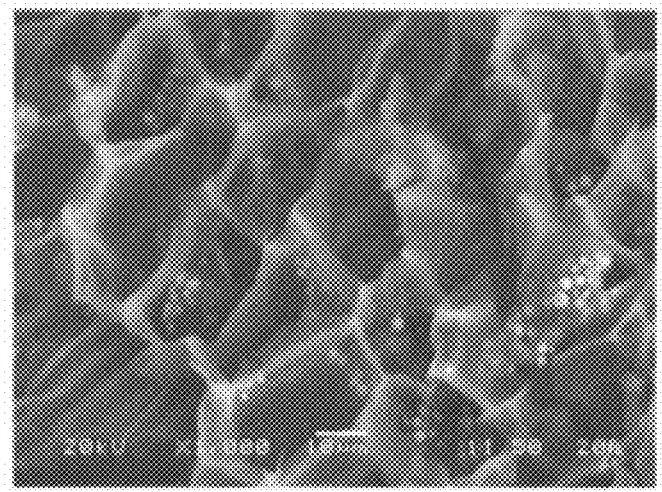
FIG. 21 shows the photograph of an aleurone layer portion of Preparation Sample 15.

Rice bran as a raw material was suspended in water and subjected to a stirrer, T. k. robomix, manufactured by Tokushu Kika Kogyo (named Primix Corporation, at present) at normal temperature (10,000 RPM, about 20 minutes) and then sieved in water using a 200 mesh (ASTM standard, sieve opening: 0.075 mm) sieve. The fraction that did not pass was recovered to remove starch. This operation was repeated twice to improve the starch removal efficiency. Furthermore, during the second operation time, a heat sterilization step at 80° C. was added. Finally, sieving was performed using a 200 mesh (ASTM standard, sieve opening: 0.075 mm) sieve. The fraction not passed was recovered and subjected to lyophilization to obtain an insoluble dietary fiber-containing product. This was designated as Preparation Sample 15. The analysis values are shown in the following Table 15. Furthermore, a scanning electron micrographic image of the aleurone layer portion contained in Preparation Sample 15 is shown in FIG. 21.

Preparation Example 16

Defatted Rice Bran→Starch Decomposition+Hemicellulase

Defatted rice bran (manufactured by Tsuno Food Industrial Co., Ltd.) was used as a raw material. A 2.0% amylase preparation (Sumiteam AS manufactured by Shinnihon Chemicals Corporation) was reacted in a 50 mM acetate buffer (pH 4.5, 65° C.) for 3 hours to decompose starch in the rice bran. After starch was decomposed, sieving was performed in water using a 200 mesh (ASTM standard, sieve opening: 0.075 mm) sieve. The fraction that did not pass was recovered and then reacted with a 1.0% hemicellulase preparation (Sumiteam NX manufactured by Shinnihon Chemicals Corporation) in a 50 mM acetate buffer (pH 4.5, 50° C.) overnight to completely decompose the aleurone layer of the plant tissue. Thereafter, sieving was performed again in water using a 200 mesh (ASTM standard, sieve opening: 0.075 mm) sieve. The fraction that did not pass was recovered and subjected to lyophilization to obtain an insoluble dietary fiber-containing product. This was designated as Preparation Sample 16. The analysis values are shown in the following Table 15.

TABLE 15

The contents of crude proteins and dietary fiber in Preparation Samples 14, 15 and 16 (wt %)

|  | Preparation Sample 14 | Preparation Sample 15 | Preparation Sample 16 |
|---|---|---|---|
| Crude proteins | 12.5 | 16.0 | 19.7 |
| Dietary fiber | 59.2 | 62.8 | 71.5 |

Test Example 8

An experiment was performed using the insoluble dietary fiber-containing products obtained in Preparation Examples 14, 15, 16 as to whether severe diarrhea and abnormality of large-intestinal mucosa caused by ulcerative colitis can be treated or not.

[Material and Method]

The test animal and method for inducing ulcerative colitis were the same as those described in Test Example 1, provided that the feed used in Test Example 8 is as shown in Table 16. The basic feed contains protein (casein) 14.6%, lipid (corn oil) 5.0%, vitamins 1.0%, minerals 3.5%, and choline chloride 0.2%. The weight is adjusted by use of cornstarch.

TABLE 16

|  | Comparative Group 15 | Experimental Group 14 | Experimental Group 15 | Experimental Group 16 |
|---|---|---|---|---|
| Casein | 14.6 | 14.0 | 13.8 | 13.8 |
| Vitamin mix[*1] | 1.0 | 1.0 | 1.0 | 1.0 |
| Mineral mix[*2] | 3.5 | 3.5 | 3.5 | 3.5 |
| Choline chloride | 0.2 | 0.2 | 0.2 | 0.2 |
| Cellulose | 3.0 | 0 | 0 | 0 |
| Preparation Sample | 0 | 5.1 | 4.8 | 4.2 |
| Dextran sulfate sodium | 3.0 | 3.0 | 3.0 | 3.0 |
| Corn oil | 5.0 | 5.0 | 5.0 | 5.0 |
| Cornstarch | 69.7 | 68.3 | 68.7 | 69.3 |

[*1]based on AIN-93
[*2]based on AIN-93

Testing Groups were set as follows:

Comparative Group 15: To the basic feed, cellulose (3.0%) was added and dextran sulfate sodium (3.0%) was added in order to induce ulcerative colitis.

Experimental Group 14: To the basic feed, Preparation Sample 14 was added to give a dietary fiber content of 3.0%, casein was added so as to adjust the protein content to 14.6%, and dextran sulfate sodium 3.0% was added in order to induce ulcerative colitis.

Experimental Group 15: To the basic feed, Preparation Sample 15 was added to give a dietary fiber content of 3.0%, casein was added so as to adjust the protein content to 14.6%, and dextran sulfate sodium 3.0% was added in order to induce ulcerative colitis.

Experimental Group 16: To the basic feed, Preparation Sample 16 was added to give a dietary fiber content of 3.0%, casein was added so as to adjust the protein content to 14.6%, and dextran sulfate sodium 3.0% was added in order to induce ulcerative colitis.

Results of Test Example 8

Figure 22:
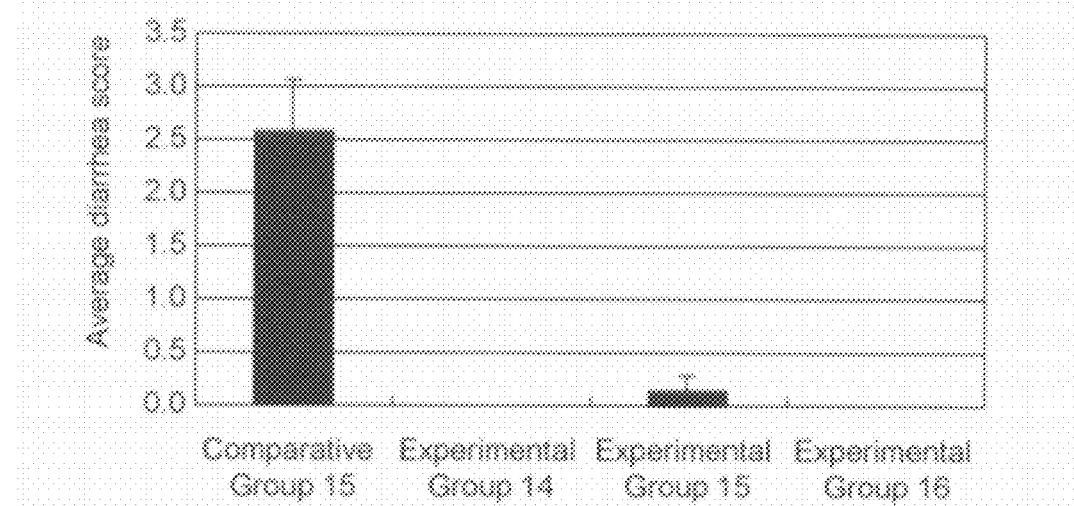
FIG. 22 shows diarrhea scores of Experimental Groups 14, 15 and 16 and Comparative Group 15.

The results are shown in FIG. 22. FIG. 22 shows the diarrhea scores of Experimental Groups 14, 15, 16 and Comparative Group 15. In FIG. 22, the diarrhea score improvement effects of Experimental Group 14, Experimental Group 15 and Experimental Group 16 were confirmed. From this, it was confirmed that Preparation Sample 14, Preparation Sample 15 and Preparation Sample 16 has a diarrhea score improvement effect. Furthermore, Preparation Sample 16 using defatted rice bran as a raw material, since lipid has previously been removed, had a high dietary fiber content compared to Preparation Sample 14 and Preparation Sample 15. Furthermore, when feed is prepared so as to have a dietary fiber content of 3.0%, Experimental Group 14 contains 5.1% of Preparation Sample 14; Experimental Group 15 contains 4.8% of Preparation Sample 15; and Experimental Group 16 contains 4.2% of Preparation Sample 16. It was found that the effect was exerted in the lowest dose in Preparation Sample 16.

Preparation Sample 15 used in Experimental Group 15, in which starch was removed only by a stirring treatment without performing an enzyme treatment, was found to have the same effect as in Preparation Sample 14 and Preparation Sample 16 in which the enzyme treatment was performed.

From these results, not only in Preparation Sample 15, in which starch alone was removed without performing an amylase and hemicellulase treatment, but also in Preparation Sample 16, in which defatted rice bran was used as a raw material, even if each of the insoluble dietary fiber-containing products was taken simultaneously with an ulcerative colitis inducing agent, it was found that the insoluble dietary fiber-containing products effectively accelerated improvement of the condition of the disease.

Preparation Example 17

Rice Bran→Starch Decomposition+Hemicellulase→Fraction that Does Not Pass through a 200 Mesh Rice bran was used as a raw material. A 2.0% amylase preparation (Sumiteam AS manufactured by Shinnihon Chemicals Corporation) was reacted in a 50 mM acetate buffer (pH 4.5, 65° C.) for 3 hours to decompose starch in the rice bran. After starch was decomposed, sieving was performed in water using a 200 mesh (ASTM standard, sieve opening: 0.075 mm) sieve. The fraction that did not pass was recovered and then reacted with a 1.0% hemicellulase preparation (Sumiteam NX manufactured by Shinnihon Chemicals Corporation) in a 50 mM acetate buffer (pH 4.5, 50° C.) overnight to completely decompose the aleurone layer of the plant tissue. Thereafter, sieving was performed again in water using a 200 mesh (ASTM standard, sieve opening: 0.075 mm) sieve. The fraction that did not pass was recovered and subjected to lyophilization to obtain an insoluble dietary fiber-containing product. This was designated as Preparation Sample 17. The analysis values are shown in Table 17 below.

Preparation Example 18

Rice Bran→Starch Decomposition+Hemicellulase→200 to 500 Mesh Fraction

Rice bran was used as a raw material. A 2.0% amylase preparation (Sumiteam AS manufactured by Shinnihon Chemicals Corporation) was reacted in a 50 mM acetate buffer (pH 4.5, 65° C.) for 3 hours to decompose starch in the rice bran. After starch was decomposed, sieving was performed in water using a 200 mesh (ASTM standard, sieve opening: 0.075 mm) sieve. The fraction that did not pass was recovered and then reacted with a 1.0% hemicellulase preparation (Sumiteam NX manufactured by Shinnihon Chemicals Corporation) in a 50 mM acetate buffer (pH 4.5, 50° C.) overnight to completely decompose the aleurone layer of the plant tissue. Thereafter, sieving was performed again in water using a 200 mesh (ASTM standard, sieve opening: 0.075 mm) sieve, the fraction passed was recovered and further sieved using a 500 mesh (ASTM standard, sieve opening: 0.025 mm) sieve. The fraction that did not pass was recovered and subjected to lyophilization to obtain an insoluble dietary fiber-containing product. This was designated as Preparation Sample 18. The analysis values are shown in Table 17.

TABLE 17

The contents of crude proteins and dietary fiber in Preparation Samples 17 and 18 (wt %)

|  | Preparation Sample 17 | Preparation Sample 18 |
|---|---|---|
| Crude proteins | 14.2 | 12.2 |
| Dietary fiber | 76.4 | 71.6 |

Test Example 9

An experiment was performed using the insoluble dietary fiber-containing product obtained in Preparation Example 17 as to whether severe diarrhea and abnormality of large-intestinal mucosa caused by ulcerative colitis can be treated or not.

[Material and Method]

Following Test Example 1, The test animal and method for inducing ulcerative colitis were the same as those described in Test Example 1, provided that the feed used in Test Example 9 is as shown in Table 18.

The basic feed contains protein (casein) 14.6%, lipid (corn oil) 5.0%, vitamins 1.0%, minerals 3.5%, and choline chloride 0.2%. The weight is adjusted by use of cornstarch.

TABLE 18

|  | Comparative Group 16 | Experimental Group 17 | Experimental Group 18 |
|---|---|---|---|
| Casein | 14.6 | 14.0 | 14.1 |
| Vitamin mix*[1] | 1.0 | 1.0 | 1.0 |
| Mineral mix*[2] | 3.5 | 3.5 | 3.5 |
| Choline chloride | 0.2 | 0.2 | 0.2 |
| Cellulose | 3.0 | 0 | 0.1 |
| Preparation Sample | 0 | 3.9 | 4.0 |
| Dextran sulfate sodium | 3.0 | 3.0 | 3.0 |
| Corn oil | 5.0 | 5.0 | 5.0 |
| Cornstarch | 69.7 | 67.3 | 69.1 |

*[1]based on AIN-93
*[2]based on AIN-93

Testing Groups were set as follows:

Comparative Group 16: To the basic feed, cellulose (3.0%) was added and dextran sulfate sodium (3.0%) was added to induce ulcerative colitis.

Experimental Group 17: To the basic feed, Preparation Sample 17 was added to give a dietary fiber content of 3.0%, casein was added so as to adjust the protein content to 14.6%, and dextran sulfate sodium 3.0% was added in order to induce ulcerative colitis.

Experimental Group 18: To the basic feed, Preparation Sample 18 was added to give a dietary fiber content of 3.0%, casein was added so as to adjust the protein content to 14.6%, and dextran sulfate sodium 3.0% was added in order to induce ulcerative colitis.

Results of Test Example 9

Figure 23:
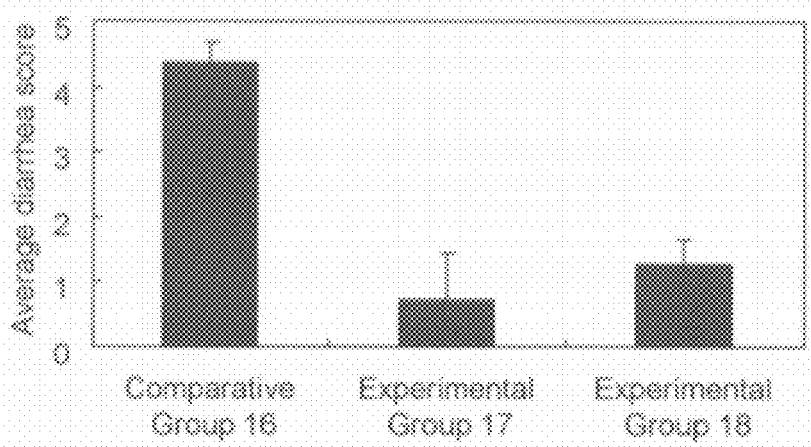
FIG. 23 shows diarrhea scores of Experimental Groups 17 and 18 and Comparative Group 16.

The results are shown in FIG. 23. FIG. 23 shows the diarrhea scores of Experimental Group 17, Experimental Group 18 and Comparative Group 16. In FIG. 23, the diarrhea score improvement effects of Experimental Group 17, Experimental Group 18 were confirmed. From this, it was confirmed that Preparation Sample 17 and Preparation Sample 18 had a diarrhea score improvement effect. However, when the diarrhea score improvement effect of Experimental Group 17 was compared with that of Experimental Group 18, it was found that Experimental Group 17 was a higher effect.

From these results, a grain size has an effect upon the degree of the effect. Since the fraction that did not pass through a 200 mesh had a higher effect than the fraction passed trough a 200 mesh, it was considered that the larger the grain size, the higher the effect.

Preparation Example 19

Rice Bran→Starch Decomposition+Hemicellulase→the Fraction that Did Not Pass 200 Mesh Defatted rice bran (manufactured by Tsuno Food Industrial Co., Ltd.) was used as a raw material. A 2.0% amylase preparation (Sumiteam AS manufactured by Shinnihon Chemicals Corporation) was reacted in a 50 mM acetate buffer (pH 4.5, 65° C.) for 3 hours to decompose starch in the rice bran. After starch was decomposed, sieving was performed in water using a 200 mesh (ASTM standard, sieve opening: 0.075 mm) sieve. The fraction that did not pass was recovered and then reacted with a 1.0% hemicellulase preparation (Sumiteam NX manufactured by Shinnihon Chemicals Corporation) in a 50 mM acetate buffer (pH 4.5, 50° C.) overnight to completely decompose the aleurone layer of the plant tissue. Thereafter, sieving was performed again in water using a 200 mesh (ASTM standard, sieve opening: 0.075 mm) sieve and then the fraction that did not pass was recovered and subjected to lyophilization to obtain an insoluble dietary fiber-containing product. This was designated as Preparation Sample 19. The analysis values are shown in Table 19 below.

Preparation Example 20

Preparation Example 19→Slightly Pulverized→Fraction that Passed through a 500 Mesh The insoluble dietary fiber-containing product obtained in Preparation Example 19 was slightly pulverized (processed by Microfoods Japan Kabushiki Kaisha) into fine powder, suspended in water and sieved in water through a 500 mesh (ASTM standard, sieve opening: 0.075 mm) sieve. The fraction passed was recovered and subjected to lyophilization to obtain an insoluble dietary fiber-containing product. This was designated as Preparation Sample 20. The analysis values are shown in the following Table 19.

TABLE 19

The contents of crude proteins and dietary fiber in Preparation Samples 19 and 20 (wt %)

| | Preparation Sample 19 | Preparation Sample 20 |
|---|---|---|
| Crude proteins | 13.74 | 14.72 |
| Dietary fiber | 76.5 | 75.9 |

Test Example 10

An experiment was performed using the insoluble dietary fiber-containing products obtained in Preparation Examples 19, 20 as to whether severe diarrhea and abnormality of large-intestinal mucosa caused by ulcerative colitis can be treated or not.

[Material and Method]

Following Test Example 1, The test animal and method for inducing ulcerative colitis were the same as those described in Test Example 1, provide that the feed used in Test Example 10 is as shown in Table 20.

The basic feed contains protein (casein) 14.6%, lipid (corn oil) 5.0%, vitamins of 1.0%, minerals 3.5%, and choline chloride 0.2%. The weight is adjusted by use of cornstarch.

TABLE 20

| | Comparative Group 17 | Experimental Group 19 | Experimental Group 20 |
|---|---|---|---|
| Casein | 14.6 | 14.1 | 14.0 |
| Vitamin mix*[1] | 1.0 | 1.0 | 1.0 |
| Mineral mix*[2] | 3.5 | 3.5 | 3.5 |
| Choline chloride | 0.2 | 0.2 | 0.2 |
| Cellulose | 3.0 | 0 | 0 |
| Preparation Sample | 0 | 3.92 | 4.0 |
| Dextran sulfate sodium | 3.0 | 3.0 | 3.0 |
| Corn oil | 5.0 | 5.0 | 5.0 |
| Cornstarch | 69.7 | 69.3 | 69.3 |

*[1]based on AIN-93
*[2]based on AIN-93

Testing Groups were set as follows:

Comparative Group 17: To the basic feed, cellulose (3.0%) was added and dextran sulfate sodium (3.0%) was added to induce ulcerative colitis.

Experimental Group 19: To the basic feed, Preparation Sample 19 was added to give a dietary fiber content of 3.0%, casein was added so as to adjust the protein content to 14.6%, and dextran sulfate sodium 3.0% was added in order to induce ulcerative colitis.

Experimental Group 20: To the basic feed, Preparation Sample 20 was added to give a dietary fiber content of 3.0%, casein was added so as to adjust the protein content to 14.6%, and dextran sulfate sodium 3.0% was added in order to induce ulcerative colitis.

Results of Test Example 10

Figure 24:
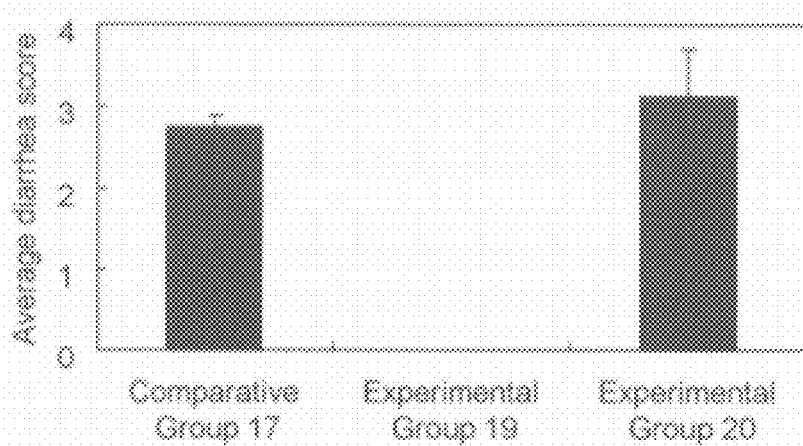
FIG. 24 shows diarrhea scores of Experimental Groups 19 and 20 and Comparative Group 17.

The results are shown in FIG. 24. FIG. 24 shows the diarrhea scores of Experimental Groups 19, 20 and Comparative Group 17. From FIG. 24, the diarrhea score improvement effect was obtained in Experimental Group 19. On the other hand, the diarrhea score improvement effect was not observed in Experimental Group 20 in which Preparation Sample 20 that was a fraction passing through a 500 mesh was used.

From the above results, it was found that the small-grain size insoluble dietary fiber-containing product of the Preparation Sample passing though a 500 mesh does not exert the effect.

Preparation Example 21

Defatted Rice Bran→Starch Decomposition+Hemicellulase)

Defatted rice bran was used as a raw material. A 1.0% amylase preparation (Sumiteam AS manufactured by Shinnihon Chemicals Corporation) was reacted for 3 hours after lactic acid was added to adjust pH (pH 4.5, 65° C.) to decompose starch in the rice bran. After starch was decomposed, sieving was performed in water using a 200 mesh (ASTM standard, sieve opening: 0.075 mm) sieve. The fraction that did not pass was recovered and then reacted with a 0.5% hemicellulase preparation (Sumiteam NX manufactured by Shinnihon Chemicals Corporation) overnight after lactic acid was added to adjust pH (pH 4.5, 50° C.) to completely decompose the aleurone layer of the plant tissue. Thereafter, sieving was performed again in water using a 200 mesh (ASTM standard, sieve opening: 0.075 mm) sieve. The fraction that did not pass was recovered and subjected to lyophilization to obtain an insoluble dietary fiber-containing product. This was designated as Preparation Sample 21. The analysis values are shown in Table 21 below.

Figure 25:
FIG. 25 shows the photograph of an aleurone layer portion contained in Preparation Sample 21.

Furthermore, a scanning electron micrographic image of the aleurone layer portion contained in Preparation Sample 21 is shown in FIG. 25.

Preparation Example 22

Defatted Rice Bran→Starch Decomposition+Hemicellulase, the Amount of Enzyme was Reduced from Preparation Example 21

Defatted rice bran was used as a raw material. A 0.5% amylase preparation (Sumiteam AS manufactured by Shinnihon Chemicals Corporation) was reacted for 3 hours after lactic acid was added to adjust pH (pH 4.5, 65° C.) to decompose starch in the rice bran. After starch was decomposed, sieving was performed in water using a 200 mesh (ASTM standard, sieve opening: 0.075 mm) sieve. Next, the fraction that did not pass was recovered and then reacted with a 0.2% hemicellulase preparation (Sumiteam NX manufactured by Shinnihon Chemicals Corporation) overnight after lactic acid was added to adjust pH (pH 4.5, 50° C.) to decompose the aleurone layer of the plant tissue and sieved in water by use of a 200 mesh (ASTM standard, sieve opening: 0.075 mm) sieve. The fraction that did not pass was recovered and subjected to lyophilization to obtain an insoluble dietary fiber-containing product.

This was designated as Preparation Sample 22. The analysis values are shown in Table 21. Furthermore, a scanning electron micrographic image of the aleurone layer portion contained in Preparation Sample 22 is shown FIG. 26.

TABLE 21

The contents of crude proteins and dietary fiber in Preparation Samples 21 and 22 (wt %)

|  | Preparation Sample 21 | Preparation Sample 22 |
| --- | --- | --- |
| Crude proteins | 13.7 | 17.2 |
| Dietary fiber | 76.5 | 73.5 |

Test Example 11

Evaluation was made as to whether severe diarrhea and abnormality of large-intestinal mucosa caused by ulcerative colitis can be treated or not with respect to Preparation Samples 21 and 22.

[Material and Method]

The test animal and method for inducing ulcerative colitis were the same as those described in Test Example 1, provided that the feed used in Test Example 11 is as shown in Table 22.

The basic feed contains protein (casein) 14.6%, lipid (corn oil) 5.0%, vitamins 1.0%, minerals 3.5%, and choline chloride 0.2%. The weight is adjusted by use of cornstarch.

TABLE 22

|  | Comparative Group 18 | Experimental Group 21 | Experimental Group 22 |
| --- | --- | --- | --- |
| Casein | 14.6 | 14.1 | 13.9 |
| Vitamin mix*[1] | 1.0 | 1.0 | 1.0 |
| Mineral mix*[2] | 3.5 | 3.5 | 3.5 |
| Choline chloride | 0.2 | 0.2 | 0.2 |
| Cellulose | 3.0 | 0 | 0.6 |
| Preparation Sample | 0 | 3.9 | 4.0 |
| Dextran sulfate sodium | 3.0 | 3.0 | 3.0 |
| Corn oil | 5.0 | 5.0 | 5.0 |
| Cornstarch | 69.7 | 69.3 | 69.3 |

*[1]based on AIN-93
*[2]based on AIN-93

Testing Groups were set as follows:

Comparative Group 18: To the basic feed, cellulose (3.0%) was added and dextran sulfate sodium (3.0%) was added to induce ulcerative colitis.

Experimental Group 21: To the basic feed, Preparation Sample 21 was added to give a dietary fiber content of 3.0%, casein was added so as to adjust the protein content to 14.6%, and dextran sulfate sodium 3.0% was added in order to induce ulcerative colitis.

Experimental Group 22: To the basic feed, Preparation Sample 22 was added in an amount of 4.0% and cellulose was added so as so as to adjust the dietary fiber content to 3.0%, casein was added so as to adjust the protein content to 14.6%, and dextran sulfate sodium 3.0% was added in order to induce ulcerative colitis.

Results of Test Example 11

Figure 26:
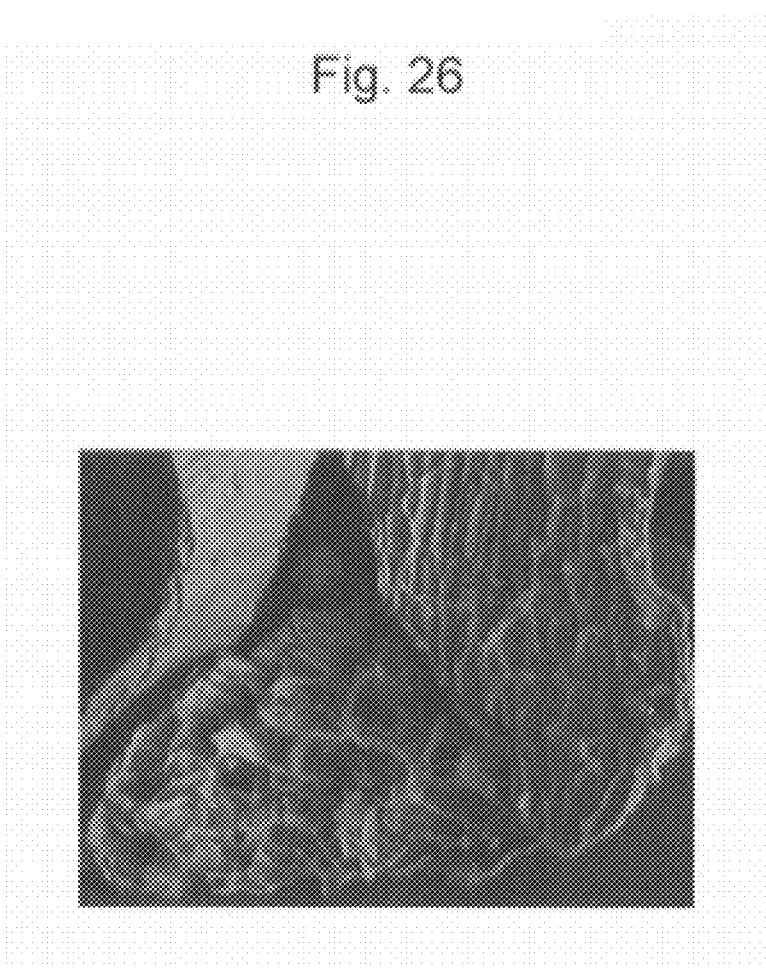
FIG. 26 shows the photograph of an aleurone layer portion contained in Preparation Sample 22.
Figure 27:
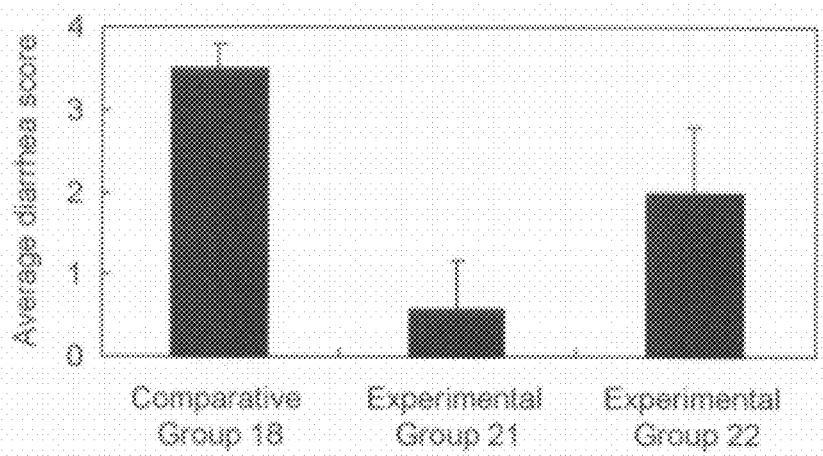
FIG. 27 shows diarrhea scores of Experimental Groups 21 and 22 and Comparative Group 18.

The results are shown in FIG. 25 to FIG. 27. FIG. 27 shows the diarrhea scores of Experimental Groups 21, 22 and Comparative Group 18. In FIG. 27, the diarrhea score improvement effect of Experimental Group 21 and Experimental Group 22 were confirmed. However, degree of the effect is higher in Experimental Group 21 than in Experimental Group 22. When FIG. 25 was compared to FIG. 26, it was observed that the remaining rate of the aleurone layer of Preparation Sample 22 is larger. This is presumed because the decomposition amount of the aleurone layer of Preparation Sample 22 with an enzyme was lower.

Preparation Example 23

Re-Treatment of Preparation Sample with Hemicellulase

Figure 28:
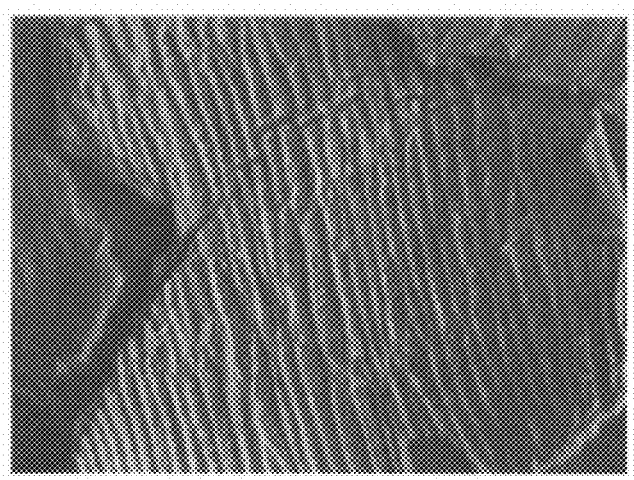
FIG. 28 shows the photograph of an aleurone layer portion contained in Preparation Sample 23.

Preparation Sample 22 was treated again with a 1.0% hemicellulase preparation (Sumiteam NX manufactured by Shinnihon Chemicals Corporation) overnight, after lactic acid was added to adjust pH (pH 4.5, 50° C.), sieved again in water through a 200 mesh (ASTM standard, sieve opening: 0.075 mm) sieve. The fraction that did not pass was recovered and subjected to lyophilization to obtain an insoluble dietary fiber-containing product. This was designated as Preparation Sample 23. The analysis value of Preparation Sample 23 is as shown in Table 23. Furthermore, a scanning electron micrographic image of the aleurone layer portion contained in Preparation Sample 23 is shown in FIG. 28.

TABLE 23

The contents of crude proteins and dietary fiber in Preparation Sample 23 (wt %)

|  | Preparation Sample 23 |
| --- | --- |
| Crude proteins | 12.4 |
| Dietary fiber | 79.9 |

Test Example 12

Evaluation was made as to whether severe diarrhea and abnormality of large-intestinal mucosa caused by ulcerative colitis can be treated or not with respect to Preparation Samples 22 and 23.
[Material and Method]
The material and experimental method were the same as those described in the aforementioned methods. The feed used in Test Example 12 is as shown in the following Table 24.

TABLE 24

|  | Comparative Group 19 | Experimental Group 22 | Experimental Group 23 |
| --- | --- | --- | --- |
| Casein | 14.6 | 13.9 | 14.1 |
| Vitamin mix*[1] | 1.0 | 1.0 | 1.0 |
| Mineral mix*[2] | 3.5 | 3.5 | 3.5 |
| Choline chloride | 0.2 | 0.2 | 0.2 |
| Cellulose | 3.0 | 0.6 | 0 |
| Preparation Sample | 0 | 4.0 | 3.8 |
| Dextran sulfate sodium | 3.0 | 3.0 | 3.0 |
| Corn oil | 5.0 | 5.0 | 5.0 |
| Cornstarch | 69.7 | 69.3 | 69.4 |

*[1]based on AIN-93
*[2]based on AIN-93

Testing Groups were set as follows:
Comparative Group 19: To the basic feed, cellulose (3.0%) was added and dextran sulfate sodium (3.0%) was added to induce ulcerative colitis.
Experimental Group 22: To the basic feed, Preparation Sample 22 was added in an amount of 4.0% and cellulose was added so as so as to adjust the dietary fiber content to 3.0%, casein was added so as to adjust the protein content to 14.6%, and dextran sulfate sodium 3.0% was added in order to induce ulcerative colitis.

Experimental Group 23: To the basic feed, Preparation Sample 23 was added to give a dietary fiber content of 3.0%, casein was added so as to adjust the protein content to 14.6%, and dextran sulfate sodium 3.0% was added in order to induce ulcerative colitis.

Results of Test Example 12

Figure 29:
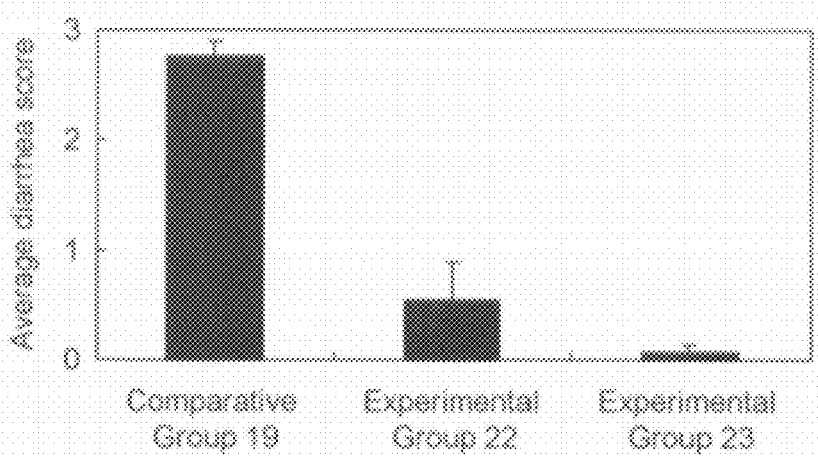
FIG. 29 shows diarrhea scores of Experimental Groups 22 and 23 and Comparative Group 19.

The results are shown in FIG. 28 and FIG. 29. FIG. 29 shows the diarrhea scores of Experimental Group 22, 23 and Comparative Group 19. From FIG. 29, the diarrhea score improvement effects of Experimental Group 22 and Experimental Group 23 were confirmed. However, the degree of the effect was higher in Experimental Group 23 than in Experimental Group 22. In FIG. 28, it was observed that the aleurone layer of Preparation Sample 23 is completely removed by decomposition. From this, it was presumed that the effect of Preparation Sample 22 increases like the effect of Preparation Sample 23.

Test Example 13

Preparation Sample 21, 22 were treated again with a 4.0% hemicellulase preparation (Sumiteam NX manufactured by Shinnihon Chemicals Corporation), in a 50 mM acetate buffer (pH 4.5, 50° C.) overnight and sieved again in water through a 200 mesh (ASTM standard, sieve opening: 0.075 mm) sieve. The fraction that did not pass was recovered and subjected to lyophilization. Thereafter, a recovery rate was calculated. Furthermore, the free amounts of arabinose and xylose, which are sugars mainly constituting the aleurone layer, were also checked in the hemicellulase treatment.

Results of Test Example 13

Figure 30:
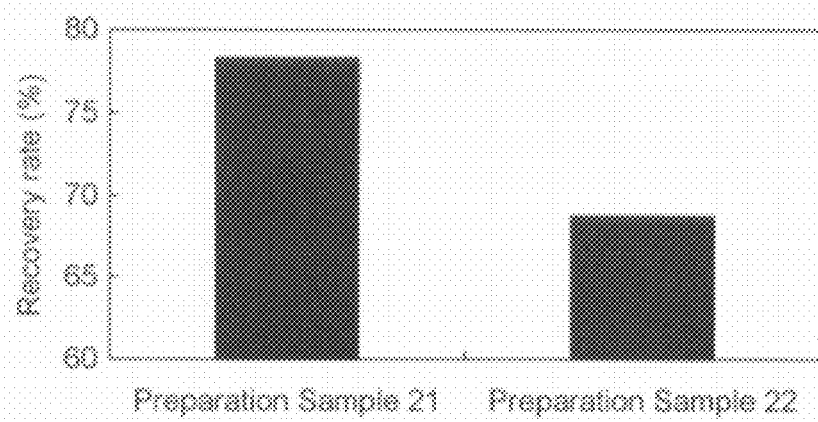
FIG. 30 shows % recovery of Preparation Samples 21 and 22 re-decomposed with enzyme.
Figure 31:
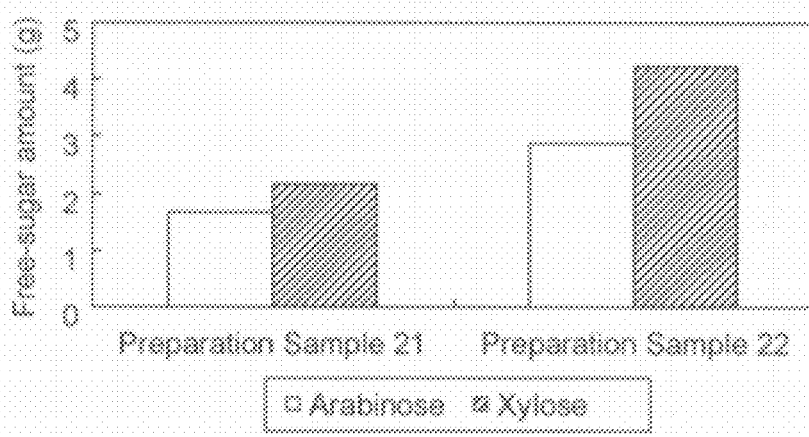
FIG. 31 shows amounts of free sugars in Preparation Samples 21 and 22 re-decomposed with enzyme.

When Preparation Sample 21 was re-decomposed with hemicellulase, a recovery rate was 78%. When Preparation Sample 22 was decomposed in the same manner, the recovery rate was 69% (FIG. 30). Furthermore, as a result that the amounts of free arabinose and xylose were checked when each sample was decomposed, it was found that the amounts of free arabinose and xylose are larger when Preparation Sample 22 is decomposed (FIG. 31). Arabinose and xylose are sugars mainly constituting the aleurone layer. From the fact that these sugars are liberated by the hemicellulase treatment, it is presumed that the aleurone layer is decomposed by the hemicellulase treatment. From the above results, the conditions in which Preparation Sample exerts an effect are presumably a recovery rate of about 70% or more, and preferably about 80% or more in re-decomposition with a hemicellulase treatment performed in the same conditions as in Test Examples. Furthermore, the degree of the aleurone layer can be expressed by the index.

INDUSTRIAL APPLICABILITY

According to the present invention, there is provided a novel material having a treatment, improvement or prevention effect on an inflammatory bowel disease such as ulcerative colitis.

The insoluble dietary fiber-containing product of the present invention, since it contains a large amount of insoluble dietary fiber derived from seeds of a grain plant(s), preferably a Gramineae plant(s), has an advantage in no side effect. The material is effectively used in a food or drink or a medicamet.

The insoluble dietary fiber-containing product of the present invention derived from seeds of a grain plant(s), preferably, a Gramineae plant(s), is effective in improving an inflammatory bowel disease, for example, preventing damage of the intestine mucosa and usefully suppressing occurrence of the accompanying diarrhea, which are severe side effects during the intake of an anticancer drug. Furthermore, the insoluble dietary fiber-containing product of the present invention can efficiently improve bowl movement of an intestinal tract excised patient and a patient with colostomy. Note that, the insoluble dietary fiber-containing product of the present invention has no side effect.

All publications, patents and JP Patent Publications (Kokai) cited in the specification are incorporated herein in its entirety by reference.

The invention claimed is:

1. A method for the treatment or prevention of ulcerative colitis, said method comprising administering a therapeutically-effective amount of an insoluble dietary fiber-containing product to a subject in need thereof, wherein the insoluble dietary fiber-containing product has 90% or more of the aleurone layer removed and wherein said product is derived from seeds of a Gramineae plant(s) and produced by a process comprising the following steps of:
   (a) preparing a raw-material by pulverizing or polishing the seeds of the Gramineae plant(s) then recovering the obtained outer fraction of the seeds;
   (b) subjecting the raw material to a starch removing treatment to prepare a starch free fraction;
   (c) enzymatically treating the fraction prepared in the step (b) with an enzyme having hemicellulase activity; and
   (d) recovering the insoluble fraction containing insoluble dietary fibers from the enzymatically treated fraction produced by step (c).

2. The method according to claim 1, wherein the Gramineae plant is rice, barley, rye or wheat.

3. The method according to claim 1, wherein, in the step (b), the starch removing treatment is carried out by an enzyme treatment using an amylase or a glucoamylase.

4. The method according to claim 1, wherein, in the step (b), the starch removing treatment is carried out by a heat gelatinization treatment.

5. The method according to claim 1, wherein, in the step (b), the starch removing treatment is carried out by a physical destruction treatment.

6. The method according to claim 5, wherein the physical destruction treatment is carried out by a homogenizer.

7. The method according to claim 1, wherein, in the step (b), the starch-free fraction is further subjected to a press-peeling treatment.

8. The method according to claim 1, wherein the raw material to be subjected to the starch removing treatment is rice bran, wheat malt, or barley malt.

9. The method according to claim 1, wherein the raw material to be subjected to the starch removing treatment is fat-free rice bran.

10. The method according to claim 8, wherein the raw material to be subjected to the starch removing treatment is wheat bran or polished-barley residue.

11. The method according to claim 7, wherein the starch-free fraction is brewer's grains.

12. The method according to claim 1, wherein, in the step (c), the enzyme having a hemicellulase activity is xylanase.

13. The method according to claim 1, wherein, in the step (c), the enzyme is used in combination with a protease.

14. The method according to claim 1, wherein, after the step (c), a defatting treatment is further comprised.

15. The method according to claim 1, wherein, the insoluble fraction in the step (d) comprises a fraction having a grain size which substantially passes through a 5 to 25 mesh American Society for Testing and Materials (ASTM) standard sieve and does not pass through a 500 mesh ASTM standard sieve.

16. The method according to claim 15, wherein the insoluble fraction in the step (d) comprises a fraction having a grain size which does not substantially pass through a 200 mesh ASTM standard sieve.

17. The method according to claim 1, wherein the insoluble dietary fiber-containing product has a protein content of 20 wt % or less and a dietary fiber content of 55 wt % or more.

18. The method according to claim 1, wherein the insoluble dietary fiber-containing product contains the insoluble dietary fiber in which the aleurone layer is completely removed.

19. The method according to claim 1, wherein the insoluble dietary fiber-containing product has the following properties:
   (i) that the insoluble dietary fiber-containing product comprises a fraction having a grain size which substantially passes through a 5 to 25 mesh American Society for Testing and Materials (ASTM) standard sieve and does not pass through a 500 mesh ASTM standard sieve;
   (ii) that the insoluble dietary fiber-containing product has a protein content of 20 wt % or less and a dietary fiber content of 55 wt % or more;
   (iii) that 90% or more of the aleurone layer of the insoluble dietary fiber has been removed; and
   (iv) that the insoluble dietary fiber-containing product has a preventative and/or an improving effect on ulcerative colitis.

20. The method according to claim 19, comprising a fraction having a grain size which does not substantially pass through a 200 mesh ASTM standard sieve.

21. A method for suppressing diarrhea resulting from ulcerative colitis, said method comprising administering a therapeutically-effective amount of an insoluble dietary fiber-containing product to a subject in need thereof, wherein the insoluble dietary fiber-containing product has 90% or more of the aleurone layer removed and wherein said product is derived from seeds of a Gramineae plant(s) and produced by a process comprising the following steps of:
   (a) preparing a raw-material by pulverizing or polishing the seeds of the Gramineae plant(s) then recovering the obtained outer fraction of the seeds;
   (b) subjecting the raw material to a starch removing treatment to prepare a starch free fraction;
   (c) enzymatically treating the fraction prepared in the step (b) with an enzyme having hemicellulase activity; and
   (d) recovering the insoluble fraction containing insoluble dietary fibers from the enzymatically treated fraction produced by step (c).

22. A method for reducing damage to the intestine mucosa resulting from ulcerative colitis, said method comprising administering a therapeutically-effective amount of an insoluble dietary fiber-containing product to a subject in need thereof, wherein the insoluble dietary fiber-containing product has 90% or more of the aleurone layer removed and wherein said product is derived from seeds of a Gramineae plant(s) and produced by a process comprising the following steps of:
   (a) preparing a raw-material by pulverizing or polishing the seeds of the Gramineae plant(s) then recovering the obtained outer fraction of the seeds;
   (b) subjecting the raw material to a starch removing treatment to prepare a starch free fraction;

(c) enzymatically treating the fraction prepared in the step (b) with an enzyme having hemicellulase activity; and
(d) recovering the insoluble fraction containing insoluble dietary fibers from the enzymatically treated fraction produced by step (c).

* * * * *